(12) United States Patent
Tracey et al.

(10) Patent No.: US 6,319,894 B1
(45) Date of Patent: Nov. 20, 2001

(54) COMPLEXES AND COMBINATIONS OF FETUIN WITH THERAPEUTIC AGENTS

(75) Inventors: Kevin Tracey, Old Greenwich, CT (US); Haichao Wang, Avenel, NJ (US)

(73) Assignee: The Picower Institute for Medical Research, Manhasset, NY (US)

( * ) Notice: Subject to any disclaimer, the term of this patent is extended or adjusted under 35 U.S.C. 154(b) by 0 days.

(21) Appl. No.: 08/780,311

(22) Filed: Jan. 8, 1997

(51) Int. Cl.[7] .................. A61K 31/167; A61K 38/17; C07K 251/74; C07K 251/86

(52) U.S. Cl. .............. 514/8; 514/261; 514/269; 514/332; 514/336; 514/345; 514/352; 514/354; 514/357; 514/615; 564/148; 564/149

(58) Field of Search .................. 514/8, 261, 262, 263, 264, 265, 266, 269, 272, 274, 332, 333, 335, 336, 338, 340, 345, 352, 354, 357, 615; 436/501, 503, 87.161; 544/264, 265, 267, 268, 269, 295, 296, 297, 298, 322, 335; 546/255, 290, 304, 314, 332; 564/47, 48, 50, 51, 148, 151, 155, 157, 227, 228, 236, 332, 149

(56) References Cited

U.S. PATENT DOCUMENTS 4,874,813 * 10/1989 O'Shannessy ............... 525/54.1
5,449,757 * 9/1995 Serrero ..................... 530/350
5,453,272 * 9/1995 Heerze et al. ............... 424/190.1
5,599,984 * 2/1997 Bianchi et al. ............... 564/157
5,750,573 * 5/1998 Bianchi et al. ............... 514/597

FOREIGN PATENT DOCUMENTS

98/30583 * 7/1998 (WO) .

OTHER PUBLICATIONS

Darnell et al. Molecular Cell Biology. New York: Scientific American Books. p. 32, 1986.*

* cited by examiner

*Primary Examiner*—Jeffrey E. Russel
(74) *Attorney, Agent, or Firm*—Piper Marbury Rudnick & Wolfe LLP; Steven B. Kelber

(57) ABSTRACT

There is disclosed a complex and a combination of the glycosylated polypeptide fetuin and a therapeutically active small molecule compound having a net positive charge at physiological pH. The presence of fetuin as a drug complex or in combination with the therapeutically active small molecule compound enhances therapeutic activity of the small molecule compound. The present invention further provides a means for screening for therapeutically active small molecule compounds by means of binding to fetuin.

9 Claims, 14 Drawing Sheets

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 359 amino acids
      (B) TYPE: amino acid
      (C) STRANDEDNESS: single
      (D) TOPOLOGY: linear (ii) MOLECULE TYPE: protein (iii) HYPOTHETICAL: no (iv) ANTI-SENSE: no (v) FRAGMENT TYPE: N-terminal fragment (vi) ORIGINAL SOURCE:
    (A) ORGANISM: human (ix) SEQUENCE DESCRIPTION: SEQ ID NO: 1:

```
Met Lys Ser Phe Val Leu Leu Phe Cys Leu Ala Gln Leu Trp Gly Cys
              5                  10                  15

His Ser Ile Pro Leu Asp Pro Val Ala Gly Tyr Lys Glu Pro Ala Cys
             20                  25                  30

Asp Asp Pro Asp Thr Glu Gln Ala Ala Leu Ala Ala Val Asp Tyr Ile
             35                  40                  45

Asn Lys His Leu Pro Arg Gly Tyr Lys His Tyr Leu Asn Gln Ile Asp
 50              55                  60

Ser Val Lys Val Trp Pro Arg Arg Pro Thr Gly Glu Val Tyr Asp Ile
 65              70                  75                  80

Glu Ile Asp Thr Leu Glu Thr Thr Cys His Val Leu Asp Pro Thr Pro
             85                  90                  95

Leu Ala Asn Cys Ser Val Arg Gln Gln Thr Gln His Ala Val Glu Gly
            100                 105                 110

Asp Cys Asp Ile His Val Leu Lys Gln Asp Gly Gln Phe Ser Val Leu
            115                 120                 125

Phe Thr Lys Cys Asp Ser Ser Pro Asp Ser Ala Glu Asp Val Arg Lys
            130                 135                 140

Leu Cys Pro Asp Cys Pro Leu Leu Ala Pro Leu Asn Asp Ser Arg Val
145                 150                 155                 160

Val His Ala Val Glu Val Ala Leu Ala Thr Phe Asn Ala Glu Ser Asn
                165                 170                 175

Gly Ser Tyr Leu Gln Leu Val Glu Ile Ser Arg Ala Gln Phe Val Pro
            180                 185                 190

Leu Pro Val Ser Val Ser Val Glu Phe Ala Val Ala Ala Thr Asp Cys
            195                 200                 205

Ile Ala Lys Glu Val Val Asp Pro Thr Lys Cys Asn Leu Leu Ala Glu
        210                 215                 220

Lys Gln Tyr Gly Phe Cys Lys Gly Ser Val Ile Gln Lys Ala Leu Gly
225                 230                 235                 240

Gly Glu Asp Val Arg Val Thr Cys Thr Leu Phe Gln Thr Gln Pro Val
                245                 250                 255

Ile Pro Gln Pro Gln Pro Asp Gly Ala Glu Ala Glu Ala Pro Ser Ala
            260                 265                 270

Val Pro Asp Ala Ala Gly Pro Thr Pro Ser Ala Ala Gly Pro Pro Val
            275                 280                 285

Ala Ser Val Val Val Gly Pro Ser Val Val Ala Val Pro Leu Pro Leu
            290                 295                 300

His Arg Ala His Tyr Asp Leu Arg His Thr Phe Ser Gly Val Ala Ser
305                 310                 315                 320

Val Glu Ser Ser Ser Gly Glu Ala Phe His Val Gly Lys Thr Pro Ile
                325                 330                 335

Val Gly Gln Pro Ser Ile Pro Gly Gly Pro Val Arg Leu Cys Pro Gly
            340                 345                 350

Arg Ile Arg Tyr Phe Lys Ile
```

355

(2) INFORMATION FOR SEQ ID NO: 2:

(i) SEQUENCE CHARACTERISTICS:
        (A) LENGTH: 367 amino acids
        (B) TYPE: amino acid
        (C) STRANDEDNESS: single
        (D) TOPOLOGY: linear (ii) MOLECULE TYPE: protein (iii) HYPOTHETICAL: no (iv) ANTI-SENSE: no (v) FRAGMENT TYPE: N-terminal fragment (vi) ORIGINAL SOURCE:
        (A) ORGANISM: human (ix) SEQUENCE DESCRIPTION: SEQ ID NO: 2:

```
Met Lys Ser Leu Val Leu Leu Cys Leu Ala Gln Leu Trp Gly Cys
                 5                  10                  15

His Ser Ala Pro His Gly Pro Gly Leu Ile Tyr Arg Gln Pro Asn Cys
                20                  25                  30

Asp Asp Pro Glu Thr Glu Glu Ala Ala Leu Val Ala Ile Asp Tyr Ile
            35                  40                  45

Asn Gln Asn Leu Pro Trp Gly Tyr Lys His Thr Leu Asn Gln Ile Asp
        50                  55                  60

Glu Val Lys Val Trp Pro Gln Gln Pro Ser Gly Glu Leu Phe Glu Ile
65                  70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
                100                 105                 110

Asp Cys Asp Phe Gln Leu Leu Lys Leu Asp Gly Lys Phe Ser Val Val
            115                 120                 125

Tyr Ala Lys Cys Asp Ser Ser Pro Asp Ser Ala Glu Asp Val Arg Lys
        130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Leu Gly Ala Pro Gly Leu
        275                 280                 285

Pro Pro Ala Gly Ser Pro Pro Asp Ser His Val Leu Leu Ala Ala Pro
```

```
                290                 295                 300
Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
                340                 345                 350

Pro Val Val Pro Pro Cys Pro Gly Arg Ile Arg His Phe Lys Val
                355                 360                 365
```

(2) INFORMATION FOR SEQ ID NO: 3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) HYPOTHETICAL: no (iv) ANTI-SENSE: no (v) FRAGMENT TYPE: fragment (vi) ORIGINAL SOURCE:
       (A) ORGANISM: uncertain (ix) SEQUENCE DESCRIPTION: SEQ ID NO: 3:

```
Pro Leu Asp Pro Val Ala Gly Tyr Lys Glu Pro Ala Xaa Asp Glu Xaa
                5                   10                  15

Glu Thr Glu Gln Ala Ala Leu Ala
            20                  24
```

(2) INFORMATION FOR SEQ ID NO: 4:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (iii) HYPOTHETICAL: no (iv) ANTI-SENSE: no (v) FRAGMENT TYPE: fragment (vi) ORIGINAL SOURCE:
       (A) ORGANISM: bovine (ix) SEQUENCE DESCRIPTION: SEQ ID NO: 4:

```
Ile Pro Leu Asp Pro Val Ala Gly Tyr Lys Glu Pro Ala Cys Asp Asp
                5                   10                  15

Pro Asp Thr Glu Gln Ala Ala Leu Ala
            20                  25
```

COMPLEXES AND COMBINATIONS OF FETUIN WITH THERAPEUTIC AGENTS

TECHNICAL FIELD OF THE INVENTION

The present invention provides a complex and a combination of the glycosylated polypeptide fetuin and a therapeutically active small molecule compound having a net positive charge at physiologic pH. The presence of fetuin as a drug complex or in combination with the therapeutically active small molecule compound enhances therapeutic activity of the small molecule compound. The present invention further provides a means for screening for therapeutically active small molecule compounds by means of binding to fetuin.

BACKGROUND OF THE INVENTION

A class of aromatic guanylhydrazones has been described in U.S. Pat. No. 5,750,573, the disclosure of which is incorporated by reference herein. These compounds have been shown to have therapeutic activity, primarily as anti-inflammatory agents. The activity is based upon an ability to suppress proinflammatory cytokine synthesis in activated macrophages and other cells. The preferred compound, called "CNI-1493" (N,N'-bis[3,5-bis[1-(aminoiminomethyl) hydrazonoethyl]phenyl]decanediamide tetrahydrochloride), inhibits TNF (tumor necrosis factor) translation and suppresses the production of IL-1, IL-6, MIP-1α and MIP-1β (proinflammatory cytokines) in human peripheral blood mononuclear cells. In vivo, CNI-1493 protects mice against lethal effects of endotoxin (lipopolysaccharide, LPS) and is anti-inflammatory as evidenced by suppression of rat paw edema and inflammation following carageenan administration. Therefore, there is always a need to improve the therapeutic properties of drug candidates such as CNI-1493 and related aromatic guanylhydrazone compounds.

Macrophages play important roles in fundamental immune protection, including, for example, phagocytosis, antigen presentation, microbiocidal and tumoricidal activities, and release of a large number of factors during host defense and inflammation. For example, upon stimulation by interferon γ (INF-γ) and potent macrophage activators such as bacterial endotoxin, macrophages secrete large amounts of reactive nitrogen intermediates (RNI), and several cytokines including TNF-α, IL-1, IL-6, MIP-1α, MIP-1β that augment the inflammatory response during bacterial infection. Generation of RNI and tumor cell killing by macrophages are both dependent on L-arginine (Keller et al., *Cancer Res.* 50:1421–1425, 1990; Hibbs et al., *J. Immunol.* 140:550–565, 1987; Drapier et al., *J. Immunol.* 140:2829–2838, 1988), a common substrate shared by arginase and nitric oxide synthase (NOS). Arginase (EC 3.5.3.1.) is an enzyme active in converting L-arginine to L-ornithine and urea, and thus plays an essential role in the urea cycle, as well as the biosynthesis of proline and polyamines (Janne et al., *Ann. Med.* 23:241, 1991). Nitric oxide synthase is an enzyme active in catalyzing the formation of nitric oxide (NO). Nitric oxide synthase is an important molecule implicated in antimicrobial, cytotoxic, and inflammatory processes mediated by macrophages, as well as in blood pressure regulation and neurotransmission in the nervous system (Hibbs et al., *Biochem. Biophys. Res. Comm.* 157:87–94, 1988; Moncada et al., *Proc. Natl. Acad. Sci. USA* 88:2166–2170, 1991, Nathan, *FASEB J.* 6:3015–3064, 1992; Moncada et al., *N. Engl. J. Med.* 329:2001–2012, 1993). Both arginase (AII) and NO synthase (iNOS) are LPS-inducible in macrophages (Granger et al., *J. Clin. Invest.* 85:264–273, 1990; Currie, *Nature* 273:758–759, 1978; Corraliza, *J. Immunol. Methods* 174:231–235, 1994; Stuehr et al., *Proc. Natl. Acad. Sci. USA* 82:7738–7742, 1985; Steuhr et al., *J. Immunol.* 139:518–525, 1987; Modlell, *Immunology Lett.* 40:139–146, 1994). Although a biological role for urea and $NO_2^-/NO_3^-$ synthesis by cells of the immune system is not yet known, it appears to represent a quantitative feature in the activation of macrophages. Arginase activity potentially controls the NO synthesis of macrophages by substrate depletion as in the absence of arginine the production of NO is dramatically reduced (Vodovotz, *J. Immunol.* 152:4110–4118, 1994). Thus, all factors controlling the relative rates of flux of L-arginine between arginase and NOS may be important in the regulation of macrophage's cytotoxic activity.

L-arginine transport in macrophages and other cells also increases in response to agents that induce iNOS (Bogel, *Biochem J.* 284:15–18, 1992; Sato et al., *Biochem. Biophys. Acta* 1069:46–52, 1991; and Cendan, *Surgery* 117:213–219, 1995). CNI-1493 and related compounds inhibit cytokine-induced arginine transport ($IC_{50}$=59 μM), and NO production ($IC_{50}$=5 μM. The cytokine-suppressive effects of CNI-1493 are possibly not mediated by inhibition of NO or L-arginine transport, nor by generalized suppression of protein synthesis or RNA synthesis.

Fetuin is a globular protein of about 60–70 kDa, containing 20–25% carbohydrate (by weight) and characterized by multiple internal disulfide bonds. The human fetuin sequence (also known as α2-HS glycoprotein) is provided herein as SEQ ID NO. 1 and SEQ ID NO. 2. Fetuin was first identified over 50 years ago as a major protein component of fetal bovine serum but its biological function remains unclear. Bovine fetuin is a globular 341-amino acid polypeptide with six internal disulfide bonds and three N-linked and two O-linked oligosaccharide chains. Primary amino acid sequence and the position of cysteine residues are well conserved in human, bovine, sheep, rat and mouse fetuin homologs (Dziegielewska et al., *J. Biol. Chem.* 265:4354, 1990; Rauth et al., *Eur. J. Biochem.* 205:321, 1992; Lee et al., *Proc. Natl. Acad. Sci. USA* 84:4403, 1987; and Brown et al., *Eur. J. Biochem.* 205:321, 1992). Fetuin levels in human plasma are regulated in a manner of a negative acute phase reactant (Lebreton et al., *J. Clin. Invest.* 64:1118, 1979). IL-1 was shown to suppress fetuin transcript levels in cultured hepatocytes (Akhoundi et al., *J. Biol. Chem.* 268:15925, 1994). Fetuin appears to be expressed in bone because transcripts have been detected in both chondrocytes and osteoblasts (Yang et al., *Bone* 12:7, 1991). The polypeptide α2-HS glycoprotein is a human homolog of fetuin and is secreted in high levels by adult liver into the peripheral circulation (Triffitt et al., *Nature* 262:226, 1976).

Human fetuin has 3 N-linked oligosaccharide chains (attached to the amine nitrogen atom of asparagine), and 2 O-linked oligosaccharide chains (attached to the oxygen atom of serine or threonine). The sugar moiety directly attached to the fetuin polypeptide is usually a N-acetylglucosamine residue. The terminal sugar residue is usually a sialic acid, in particular a N-acetylneuraminic acid (NANA) residue, which bears a net negative charge. If one removes the terminal sialic acid residue from fetuin by neuraminidase treatment, the resulting glycoprotein is an asialofetuin. Fetuin is a carrier protein for growth factors, and human fetuin is sometimes referred to as α2-HS-glycoprotein. Thus, it is considered that fetuin's biological effects on cultured cells are related to its carrier function for molecules with growth-promoting properties. Fetuin is secreted by adult liver into the peripheral circulation and accumulates to high levels in bone.

The synthesis of human α2-HS-glycoprotein is down-regulated by cytokines (hIL-1β, hIL-6) (Lebreton et al., *J. Clin. Invest.* 64:1118–1129, 1979). Human fetuin levels are decreased (25–50%) in trauma patients (van Oss et al., *J. Trauma* 15:451, 1975). Therefore, there is a need in the art to find a utility for fetuin and to understand fetuin's physiological role and the importance of its many negatively charged (at physiologic pH) sialic acid residues.

SUMMARY OF THE INVENTION

The present invention provides a complex of a glycosylated polypeptide selected from the group consisting of a mammalian fetuin, α2-HS glycoprotein, and combinations thereof; and a positively charged (at physiologic pH) therapeutic compound selected from the formula:

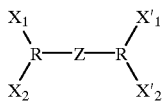

wherein R is independently selected from the group consisting of phenyl, pyridine, amino-substituted pyridine, purine, oxo-substituted purine, $C_{1-6}$ alkyl-substituted purine, xanthine, pyrimidine, $C_{1-6}$ alkyl-substituted pyrimidine, and oxo-substituted pyrimidine; wherein $X_2$ is selected from the group consisting of $H_2N(CNH)$—NH—N=CH—, $H_2N(CNH)$—NH—N=C(CH$_3$)—, and H—; wherein $X_1$, $X'_1$ $X'_2$ are independently selected from the group consisting of $H_2N(CNH)$—NH—N=CH— and $H_2N(CNH)$—NH—N=C(CH$_3$)—; wherein Z is selected from the group consisting of phenyl, pyridyl (C$_5$NH$_3$), —NH(CO)NH—, straight or branched $C_{2-10}$ alkyl, straight or branched $C_{2-10}$ alkenyl, —A— straight or branched $C_{2-10}$ alkyl —A—, —A— straight or branched $C_{2-10}$ alkenyl —A—, and —A—, wherein A is independently selected from the group consisting of —NH(CO)—, —(CO)NH—, —NH(CO)NH—, —NH—, and —O—. Preferably, the glycosylated polypeptide is human fetuin. Preferably, $X_1$, $X'_1$, $X_2$ and $X'_2$ are each $H_2N(CNH)$—NH—N=C(CH$_3$)—.

The present invention further provides a pharmaceutical composition comprising:

(A) an active component consisting essentially of a glycosylated polypeptide selected from the group consisting of a mammalian fetuin, α2-HS glycoprotein, and combinations thereof; and (B) a positively charged (at physiologic pH) therapeutic compound selected from the formula:

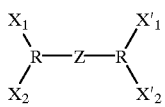

wherein R is independently selected from the group consisting of phenyl, pyridine, amino-substituted pyridine, purine, oxo-substituted purine, $C_{1-6}$ alkyl-substituted purine, xanthine, pyrimidine, $C_{1-6}$ alkyl-substituted pyrimidine, and oxo-substituted pyrimidine; wherein $X_2$ is selected from the group consisting of $H_2N(CNH)$—NH—N=CH—, $H_2N$ (CNH)—NH—N=C(CH$_3$)—, and H—; wherein $X_1$, $X'_1$ $X'_2$ are independently selected from the group consisting of $H_2N(CNH)$—NH— N=CH—and $H_2N(CNH)$—NH—N=C(CH$_3$)—; wherein Z is selected from the group consisting of phenyl, pyridyl (C$_5$NH$_3$), —NH(CO)NH—, straight or branched $C_{2-10}$ alkyl, straight or branched $C_{2-10}$ alkenyl, —A— straight or branched $C_{2-10}$ alkyl —A—, —A— straight or branched $C_{2-10}$ alkenyl —A—, and —A—, wherein A is independently selected from the group consisting of —NH(CO)—, —(CO)NH—, —NH(CO)NH—, —NH—, and —O—; and (C) a pharmaceutially acceptable carrier.

Preferably, the glycosylated polypeptide is human fetuin. Preferably, $X_1$, $X'_1$, $X_2$ and $X'_2$ are each NH$_2$(CHN)—NH—N=C(CH$_3$)—.

The present invention further provides a therapeutic combination of a glycosylated polypeptide and a positively charged (at physiologic pH) therapeutic compound:

wherein the glycosylated polypeptide is selected from the group consisting of a mammalian fetuin, α2-HS glycoprotein, and combinations thereof; and wherein the positively charged (at physiologic pH) therapeutic compound selected from the formula:

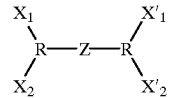

wherein R is independently selected from the group consisting of phenyl, pyridine, amino-substituted pyridine, purine, oxo-substituted purine, $C_{1-6}$ alkyl-substituted purine, xanthine, pyrimidine, $C_{1-6}$ alkyl-substituted pyrimidine, and oxo-substituted pyrimidine; wherein $X_2$ is selected from the group consisting of $H_2N(CNH)$—NH—N=CH—, $H_2N$ (CNH)—NH—N=C(CH$_3$)—, and H—;

wherein $X_1$, $X'_1$ $X'_2$ are independently selected from the group consisting of $H_2N(CNH)$—NH— N=CH— and $H_2N(CNH)$—NH—N=C(CH$_3$)—; wherein Z is selected from the group consisting of phenyl, pyridyl (C$_5$NH$_3$), —NH(CO)NH—, straight or branched $C_{2-10}$ alkyl, straight or branched $C_{2-10}$ alkenyl, —A— straight or branched $C_{2-10}$ alkyl —A—, —A— straight or branched $C_{2-10}$ alkenyl —A—, and —A—, wherein A is independently selected from the group consisting of —NH(CO)—, —(CO)NH—, —NH(CO)NH—, —NH—, and —O—. Preferably, the glycoslylated polypeptide in human fetuin. Preferably, $X_1$, $X'_1$, $X_2$ and $X'_2$ are each $H_2N(CNH)$—NH—N=C(CH$_3$)—.

The present invention further provides a method for finding therapeutically active small molecule compounds having a net positive charge at physiologic pH, comprising:

(a) providing a mammalian fetuin glycoprotein or a combination of fetuin glycoproteins in a buffer solution at physiologic pH, wherein the fetuin glycoprotein oligosaccharide moieties contain a plurality of sialic acid residues;

(b) contacting a small molecule compound in solution or a library of multiple small molecule compounds in solution to the fetuin glycoprotein at physiologic pH; and (c) measuring whether the small molecule compound or a small molecule compound from the library of small molecule compounds had bound to the fetuin glycoprotein.

Preferably, the fetuin glycoprotein is bound to a solid substrate support. Preferably, the fetuin glycoprotein has a human sequence.

BRIEF DESCRIPTION OF THE DRAWINGS

FIG. 2 specifically shows therapeutic activity of CNI-1493 in non-responsive cell cultures only when the supernatant fraction ("+F") from responsive cell cultures was added. The therapeutic activity measured was inhibition of the TNF response to LPS (endotoxin) challenge.

DETAILED DESCRIPTION OF THE INVENTION

Figure 1:
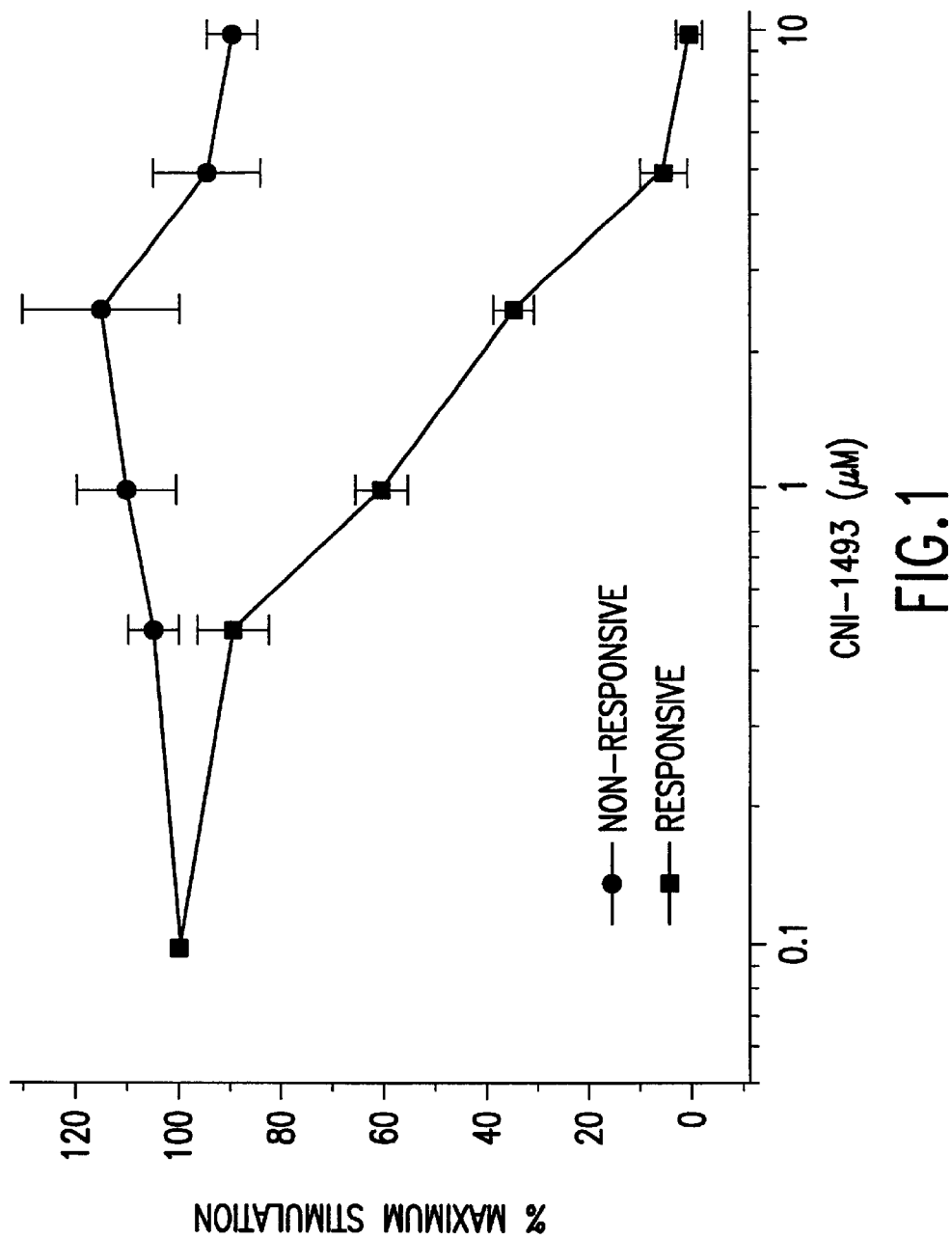
FIG. 1 shows an initial finding that launched the investigation detailed in the Examples section. Specifically, RAW 264.7 cells (murine macrophage-like cells) precultured under low serum conditions were not responsive to treatment with compound CNI-1493 (N,N'-bis[3,5-bis[1-(aminoiminomethyl)hydrazonoethyl]phenyl]decanediamide tetrahydrochloride). An indication of non-responsiveness is a failure by compound CNI-1493 to inhibit TNF (tumor necrosis factor) levels in culture supernatants in response to LPS (endotoxin or lipopolysaccharide) challenge.

The present invention provides a combination and a complex of a glycosylated polypeptide selected from the group consisting of a mammalian fetuin, α2-HS glycoprotein, and combinations thereof; and a positively charged (at physiologic pH) therapeutic compound selected from the formula:

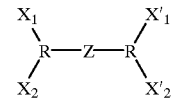

wherein R is independently selected from the group consisting of phenyl, pyridine, amino-substituted pyridine, purine, $C_{1-6}$ alkyl-substituted purine, oxo-substituted purine, xanthine, pyrimidine, $C_{1-6}$ alkyl-substituted pyrimidine, and oxo-substituted pyrimidine; wherein $X_2$ is selected from the group consisting of $H_2N(CNH)$—NH—N=CH—, $H_2N(CNH)$—NH—N=C($CH_3$)—, and H—;

wherein $X_1$, $X'_1$, $X'_2$ are independently selected from the group consisting of $H_2N(CNH)$—NH—N=CH— and $H_2N(CNH)$—NH—N=C($CH_3$)—; wherein Z is selected from the group consisting of phenyl, pyridyl ($C_5NH_3$), —NH(CO)NH—, straight or branched $C_{2-10}$ alkyl, straight or branched $C_{2-10}$ alkenyl, —A— straight or branched $C_{2-10}$ alkyl —A—, —A— straight or branched $C_{2-10}$ alkenyl —A—, and —A—, wherein A is independently selected from the group consisting of —NH(CO)—, —(CO)NH—, —NH(CO)NH—, —NH—, and —O—. Preferably, the glycosylated polypeptide is human fetuin. Preferably, $X_1$, $X'_1$, $X_2$ and $X'_2$ are each $H_2N(CNH)$—NH—N=C($CH_3$)—.

In RAW 264.7 macrophages, lipopolysaccharide (LPS) substantially stimulates production of NO, urea, and pro-inflammatory cytokine TNF-α over baseline control levels. CNI-1493 is a tetravalent guanylhydrazone-substituted aromatic compound that promotes a dose-dependent suppression of urea, NO, and TNF-α production from the LPS-activated macrophages. However, when RAW 264.7 macrophages cells were pre-cultured under low-serum conditions or for several days without replenishment with fresh serum-containing medium, their response to CNI-1493 was markedly impaired, although their response to LPS was not affected. Such cell cultures are called "non-responsive" cell cultures because they did not respond to the therapeutic activity of CNI-1493 but did respond to endotoxin. When given concurrently with CNI-1493, a 30–100 kDa protein fraction obtained from CNI-1493-responsive cells, or from culture medium conditioned by such responsive cells, using a selective ultrafiltration protocol dose-dependently increased CNI-1493-mediated inhibition of urea, NO, and TNF production from LPS-activated macrophage cultures. This CNI-1493-enhancing activity or "factor" was found to accumulate in RAW 264.7 cell-conditioned media, with a substantial increase by 4 hours in the presence of LPS at 1 μg/ml. Further fractionation by ion-exchange chromatography, and SDS-PAGE gel revealed that the CNI-1493-enhancing activity associated with a ~60–70 kDa protein that was eluted from an anion exchange column in high-salt fractions. These results indicated involvement of a macrophage-secreted protein in an inactivation of LPS-stimulated RAW 264.7 macrophages by CNI-1493.

A 30–100 kDa fraction from RAW 264.7 macrophage culture supernatants, cultured under normal conditions ("responsive cells") potentiated the cells' ability to respond to CNI-1493. A similar 30–100 kDa fraction from macrophage RAW 264.7 cell culture supernatants, cultured under low-serum or serum-depleted conditions ("non-responsive cells"), failed to potentiate the cells' ability to respond to CNI-1493. These data indicated that a CNI-1493-mediated signaling pathway might be impaired in RAW 264.7 macrophages cultured under low-serum conditions.

The CNI-1493-effect-enhancing activity was isolated from macrophage whole-cell lysates by ultrafiltration with membranes with defined Mr cut-off ranges. Ultrafiltration of whole-cell lysate on membranes with Mr cut-off of 100,000 daltons (Centricon®-100) distributed CNI-1493-effect-enhancing activity predominantly to the filtrate. Subsequent ultrafiltration of this filtrate on a membrane with a Mr cut-off of 30,000 dalton distributed CNI-1493-enhancing activity entirely to the retentate fraction (that is, the 30–100 kDa fraction). These data suggested that CNI-1493-effect-enhancing activity existed as a molecular species with a native molecular weight less than 100 kDa but greater that 30 kDa.

The CNI-1493-enhancing activity was released from macrophage cell cultures into the medium. In minimal medium (OPTI-MEM) conditioned by RAW 264.7 macrophages, CNI-1493-enhancing activity was detected by as early as 2 hours in a 30–100 kDa fraction. A further increase of the CNI-1493-enhancing activity in RAW 264.7-conditioned medium was seen by 4 hours in the presence of LPS. Four hours after LPS stimulation, a corresponding decrease of CNI-1493-enhancing activity was detected in the 30–100 kDa intracellular fraction. These data indicate that protein(s) contributing to CNI-1493-enhancing activity are released or secreted into the medium, and this accumulation is further stimulated by treatment with bacterial endotoxin (LPS).

The 30–100 kDa fraction (obtained from the above-described ultrafiltration process) was further purified by ion-exchange chromatography. The protein(s) contributing to CNI-1493-effect-enhancing activity in the macrophage intracelluar and extracellular fraction were the same protein (s) because: i) the proteins coeluted at an identical concentration range (1.8–2.0 M) of a linear salt gradient from a cationic (MONO-Q™) ion exchange column; and ii) the proteins were identified with specific polypeptide bands that co-migrated upon SDS-PAGE analysis and which also correlated with the fraction exhibiting enhancement if CNI-1493 therapeutic activity among the MONO-Q™ fractions.

Further N-terminal sequence analysis of the protein and comparison to existing databases revealed that the protein of interest had a sequence similar to bovine fetuin.

CNI-1493 is a tetravalent guanylhydrazone compound (N, N'-bis[3,5-bis[1-(aminoiminomethyl)hydrazonoethyl] phenyl]decanediamide tetrahydrochloride) that carries four positive charges at physiological pH. CNI-1493 suppresses LPS-induced production of cytokines, NO, and urea from LPS-activated macrophages. Without being bound by any particular theory, explanation, or proposed mechanism of action, plausible hypotheses of the mechanism of action of CNI-1493 and the activity potentiation by a complex or combination with fetuin and similar sialic acid-containing glycoproteins may be set forth. For example, i) macrophages can release negatively-charged glycoprotein factors that can act to potentiate CNI-1493 therapeutic activity; ii) cell membranes can bind CNI-1493 and fetuin in complex or combination, which complex or combination then transduces signal to the cell. Signal is transduced either through having the complex or the CNI-1493 small molecule compound bind a specific receptor on the cytoplasmic cell membrane, or through facilitory uptake of CNI-1493 into the target cell.

Macrophage effector functions are highly regulated, presumably to limit damage to normal tissues. In the context of cell-mediated reactivity to ongoing invasive or inflammatory stimulation, as occurs in chronic infection, both positive and negative macrophage stimuli may be generated. CNI-1493 likely negatively regulates an LPS-responsive macrophage activation pathway. Macrophages can release negatively charged protein factors that potentiate CNI-1493 enhancing activity, possibly by binding to the polycationic compound and facilitating its presentation to a cell or to an intracellular signaling pathway of a cell.

Pharmaceutical Composition

The present invention further provides a pharmaceutical composition comprising:

(A) an active component consisting essentially of a glycosylated polypeptide selected from the group consisting of a mammalian fetuin, α2-HS glycoprotein, and combinations thereof; and (B) a positively charged (at physiologic pH) therapeutic compound selected from the formula:

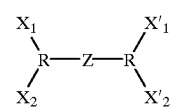

wherein R is independently selected from the group consisting of phenyl, pyridine, amino-substituted pyridine, purine, oxo-substituted purine, $C_{1-6}$ alkyl-substituted purine, xanthine, pyrimidine, $C_{1-6}$ alkyl-substituted pyrimidine, and oxo-substituted pyrimidine; wherein $X_2$ is selected from the group consisting of H₂N(CNH)—NH—N=CH—, H₂N (CNH)—NH—N=C(CH₃)—, and H—;
wherein X₁, X'₁ X'₂ are independently selected from the group consisting of H₂N(CNH)—NH—N=CH— and H₂N(CNH)—NH—N=C(CH₃)—; wherein Z is selected from the group consisting of phenyl, pyridyl (C₅NH₃), —NH(CO)NH—, straight or branched C₂₋₁₀ alkyl, straight or branched C₂₋₁₀ alkenyl, —A— straight or branched C₂₋₁₀ alkyl —A—, —A— straight or branched C₂₋₁₀ alkenyl —A—, and —A—, wherein A is independently selected from the group consisting of —NH(CO)—, —(CO)NH—, —NH(CO)NH—, —NH—, and —O—; and (C) a pharmaceutically acceptable carrier.

Preferably, the glycosylated polypeptide is human fetuin. Preferably, X₁, X'₁, X₂ and X'₂ are each NH₂(CHN)—NH—N=C(CH₃)—.

The present invention further provides a therapeutic combination of a glycosylated polypeptide and a positively charged (at physiologic pH) therapeutic compound:
 wherein the glycosylated polypeptide is selected from the group consisting of a mammalian fetuin, α2-HS glycoprotein, and combinations thereof; and
 wherein the positively charged (at physiologic pH) therapeutic compound selected from the formula:

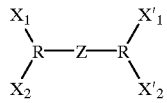

wherein R is independently selected from the group consisting of phenyl, pyridine, amino-substituted pyridine, purine, oxo-substituted purine, C₁₋₆ alkyl-substituted purine, xanthine, pyrimidine, C₁₋₆ alkyl-substituted pyrimidine, and oxo-substituted pyrimidine; wherein X₂ is selected from the group consisting of NH₂(CHN)—NH=CH—, NH₂(CHN)—NH—N=C(CH₃)—, and H—;
wherein X₁, X'₁ and X'₂ are independently selected from the group consisting of NH₂(CHN)—NH=CH—, and NH₂(CHN)—NH—N=C(CH₃)—; wherein Z is selected from the group consisting of phenyl, pyrimidine (C₅NH₃), —NH(CO)NH—, straight or branched C₂₋₁₀ alkyl, straight or branched C₂₋₁₀ alkenyl, —A— straight or branched C₂₋₁₀ alkyl —A—, —A— straight or branched C₂₋₁₀ alkenyl —A—, and —A—, wherein A is independently selected from the group consisting of —NH(CO)—, —(CO)NH—, —NH(CO)NH—, —NH—, and —O—. Preferably, the glycosylated polypeptide is human fetuin. Preferably, X₁, X'₁, X₂ and X'₂ are each NH₂(CHN)—NH—N=C(CH₃)—.

Pharmaceutical Formulations

The inventive pharmaceutical complex or inventive pharmaceutical combination can be administered to a patient either by itself (complex or combination) or in pharmaceutical compositions where it is mixed with suitable carriers and excipients. The inventive complex or combination can be administered parenterally, such as by intravenous injection or infusion, intraperitoneal injection, subcutaneous injection, or intramuscular injection. The inventive complex or combination can be administered orally or rectally through appropriate formulation with carriers and excipients to form tablets, pills, capsules, liquids, gels, syrups, slurries, suspensions and the like. The inventive complex or combination can be administered topically for various dermatologic disorders where an anti-inflammatory agent is appropriate. The inventive complex or combination is formulated into topical creams, liquids or gels suitable to topical application to skin or mucosal membrane surfaces. The inventive complex or combination can be administered by inhaler to the respiratory tract for local treatment of various respiratory inflammatory diseases.

The dosage of the inventive complex or combination suitable for use with the present invention can be determined by those skilled in the art from this disclosure. The pharmaceutical composition will contain an effective dosage (depending upon the route of administration and pharmacokinetics of the active agents) of the inventive complex or combination and suitable pharmaceutical carriers and excipients, which are suitable for the particular route of administration of the formulation (i.e., oral, parenteral, topical or by inhalation). The active complex or combination is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the active complex or combination in water-soluble form. Additionally, suspensions of the active complex or combination may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

Pharmaceutical formulations for oral administration can be obtained by combining the active complex or combination with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelatin, gums, or polyvinylpyrrolidone. In addition, a disintegrating agent may be added, and a stabilizer may be added.

Research Applications

The present invention further provides a method for finding therapeutically active small molecule compounds having a net positive charge at physiological pH, comprising:
 (a) providing a mammalian fetuin glycoprotein or a combination of mammalian fetuin glycoproteins in a buffer solution at physiologic pH, wherein the fetuin glycoprotein oligosaccharide moieties contain a plurality of sialic acid residues;
 (b) contacting a small molecule compound in solution or a library of multiple small molecule compounds in solution to the fetuin glycoprotein at physiologic pH; and
 (c) measuring whether the small molecule compound or a small molecule compound from the library of small molecule compounds had bound to the fetuin glycoprotein. Preferably, the fetuin glycoprotein is bound to a solid support matrix to provide for better isolation and a determination of fetuin binding to a candidate compound. The amino acid sequence for human fetuin glycoprotein is found in SEQ ID NO: 1 and SEQ ID NO: 2. The binding assay is useful to screen potential drug compounds whose therapeutic activity can by augmented by either co-administration with fetuin or by forming a drug-fetuin complex prior to administration.

EXAMPLE 1

This example illustrates the initial observation that there are macrophage-like cell cultures which are responsive and those that are non-responsive to the therapeutic effects of compound CNI-1493. Prior studies have demonstrated that pre-treatment of RAW 264.7 cell cultures with CNI-1493 suppresses LPS-stimulated production of urea, NO, TNF, and several other cytokines such as IL-1 β, IL-6, MIP-1α, and MIP-1β. The effect of CNI-1493 on inducible arginase and iNOS activity was investigated, because arginase and inducible nitric oxide synthase (iNOS) activity in macrophages have been posited to play important roles in the pathogenesis of human disease, and can be stimulated by potent inflammatory agents, such as bacterial lipopolysaccharide (LPS).

RAW 264.7 murine macrophages were obtained from the American Tissue Culture Collection (ATCC), and cultured in RPMI 1640 containing 10% fetal bovine serum (FBS) and 2 mM glutamine at 37° C. under a 5% $CO_2$:95% air atmosphere. Typically, cultures were maintained in 150-mm plates with 30 mls culture medium until they reached 80–90% confluence, and were then subjected to different experimental protocols. Typically, cultures were split at 1:4 and first cultured in RPMI 1640 containing 10% FBS/1% glutamine for 24 hours. Subsequently, the spent medium was replaced by fresh medium (RPMI 1640) containing 5% FBS/1% glutamine to create "serum-depleted" or "low-serum" cultures. The incubation was continued for another 24 hours before subjecting the cultures to further experiments. Alternatively, non-responsive cultures were prepared by culturing freshly spit subcultures for several days without replenishment of serum-containing medium, over which period the cultures progressively became less responsive to CNI-1493. By about four days post-subculturing, the cultures were non-responsive to CNI-1493.

RAW 264.7 cells from responsive or non-responsive cultures were harvested for experimental use by gentle scraping, washed, resuspended in RPMI 1640/10% FBS/1% glutamine at $10^6$ cell per ml in 24-well tissue culture plates, and precultured for 2 hours at 37° C. in 5% $CO_2$:95% air to allow the cells to readhere. LPS (endotoxin) was sonicated for 10 minutes and added to culture media to achieve the desired final concentration, typically 100 ng/ml. Drug (e.g., CNI-1493) was added to the medium one hour before LPS. Test fractions or experimental compounds or protein mixtures (e.g., those containing fetuin) were added concurrently with drug in RPMI 1640 medium containing 10% fetal bovine serum and 1% glutamine. Urea and NO concentrations in culture supernatants were assayed 20 hours after LPS treatment; TNF concentrations were typically assayed 4 hours after LPS treatment.

Accumulation of urea in the cell culture medium was measured as a functional assay of LPS-inducible arginase II activity. Urea concentrations were measured spectrophotometrically using Sigma Diagnostics Urea Nitrogen reagents as instructed by the manufacturer (Ca. No. 535-A, Sigma, St. Louis, Mo. USA). The optical density at 535 nm was measured, and urea concentrations were calculated by comparison with $OD_{535}$ of standard dilutions of urea prepared in culture medium. Percent of inhibition (I) for urea production was calculated by the formula, $I=100\times(A-B)/A$, where A and B are the urea concentrations corresponding to treatment with either LPS alone, or LPS plus CNI-1493, respectively.

Inducible nitric oxide synthase activity (iNOS) was assayed indirectly by measuring $NO^{2-}$ production. $NO^{2-}$ was measured by a colorimetric assay based on the Griess reaction. Briefly, 100 µl aliquots of macrophage-conditioned medium were incubated with 900 µl aliquots of Griess reagent (1% sulfanilamide/0.1% naphthylethylene diamine dihydrochloride/2.5% $H_3PO_4$). The optical density was read at 560 nm after 10 min, and $NO^{2-}$ concentration was determined with reference to a standard curve by using concentrations of 1.5 to 50 µM sodium nitrite in culture medium.

TNF concentrations were determined on the supernatants collected from stimulated RAW 264.7 cell cultures four hours after LPS stimulation by ELISA (Genzyme) performed in 96-well microtiter plates as advised by the manufacturer (the minimum detectable concentration [MDC]=10 pg/ml).

In "responsive" cultures, addition of CNI-1493 promoted a dose-dependent suppression of urea production by LPS-stimulated RAW 264.7 cell cultures. Approximately 5 µM was the CNI-1493 dose associated with a >95% decrease in urea accumulation compared to control (p<0.01). The $IC_{50}$ (concentration of 50% inhibition) of CNI-1493 with respect to urea production was estimated to be <2.0 µM, approximately the same as $IC_{50}$ values estimated for CNI-1493 with respect to NO and TNF production in responsive cultures. An assay for arginine uptake found the $IC_{50}$ for CNI-1493 to be about 10 µM. The level of urea and nitrite produced by LPS-activated macrophage cultures correlated well to level of TNF. Thus, the level of urea and nitrite produced from LPS-activated macrophages was employed as a useful index of LPS-inducible arginase and iNOS activity, and the state of LPS-induced macrophage activation when compared with appropriate controls.

When RAW 264.7 macrophage cultures were cultured in RPMI-1640 medium containing 10% FBS/1% glutamine for extended periods of time (≧56 hours after 1:4 split as opposed to <48 hours, for example), significant levels of urea, NO, and TNF were still produced by LPS-activated macrophages. However, the levels of urea, NO, and/or TNF were not reduced when CNI-1493 was added, even at a concentration as high as 5 µM. Such macrophage cultures that failed to respond to CNI-1493 ("CNI-1493 non-responsive cell cultures") retained their ability to respond to LPS, as they accumulated the same concentrations of urea, NO, and TNF-α after LPS stimulation as did shorter term cultures. A comparison of responsive and non-responsive RAW 264.7 cell cultures is provided in FIG. 1, showing the response to different concentrations of the drug compound, CNI-1493.

We tested if we could reproduce the above phenomenon by manipulating the serum concentration of the medium in which RAW 264.7 macrophages were precultured. Preculturing the RAW 264.7 cells for one day in medium containing 5% FBS substantially affected the response of the cultures to CNI-1493, but not to LPS. At 2.5 µM, CNI-1493 caused a less than 10% suppression of urea, NO, and TNF accumulation in the "serum-starved" macrophage cultures, as opposed to a larger than 50% suppression of urea and NO, and >90% suppression of TNF production, from responsive cell cultures that were maintained with higher serum concentrations. These data suggest that serum-starvation affected the response of RAW 264.7 macrophage cell cultures to CNI-1493, but not their response to LPS treatment.

EXAMPLE 2

Figure 4:
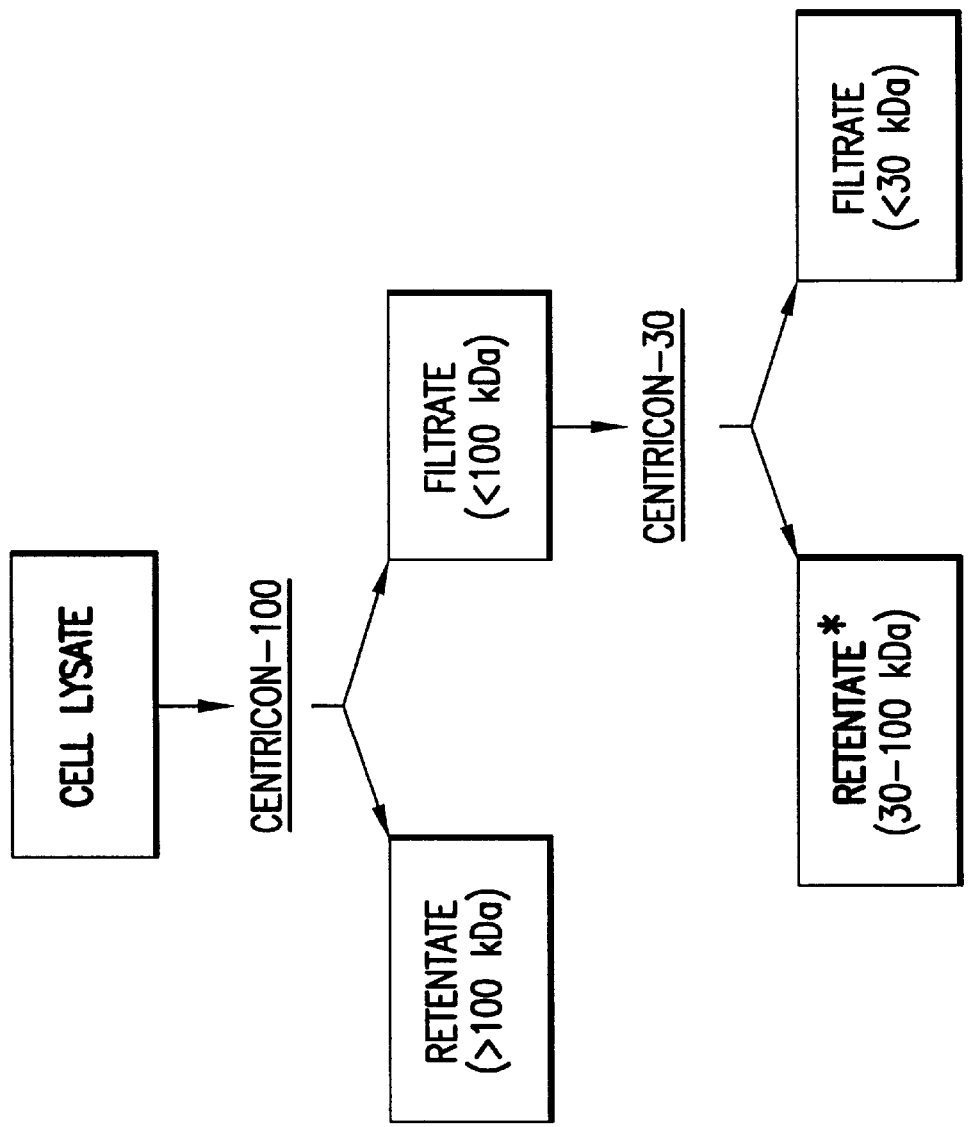
FIG. 4 shows a purification scheme used to isolate the CNI-1493 activity-enhancing activity or "factor" (i.e., fetuin) responsible for making non-responsive cell cultures responsive.

This example illustrates a procedure used to discover that fetuin was the protein responsible for restoring non-responsive macrophage cell cultures to a responsive state with respect to the therapeutic activity of CNI-1493. The fractionation scheme used is shown in FIG. 4. Cells from responsive RAW 264.7 cell cultures were harvested by gentle scraping and washed three times in phosphate buffer saline (PBS), collected by centrifugation (1000 rpm, 10 min. at 4° C.), and subjected to three rounds of freeze-thaw cycles to lyse the cells. Whole-cell lysate preparations were fractionated by sequential ultrafiltration over Amicon Centricon®-100, and Centricon®-30 filters, respectively. Different fractions, including a filtrate of Centricon®-100 and the subsequent retentate of Centricon®-30, were then assayed for biological activity with respect to the production of urea, NO, and TNF from LPS-stimulated macrophage cultures also treated with CNI-1493, described in Example 1. CNI-1493-effect-enhancing activity was detected in terms of arginase activity, 1 Unit of arginase activity representing the amount of activity necessary to produce 2 picomole of urea/16 hour/$10^6$ cells.

Ultrafiltration of RAW 264.7 macrophage cultures whole-cell lysate eliminated the vast majority (>90%) of proteins in the macrophage whole-cell lysate. When added concurrently with CNI-1493, the retentate of Centricon®-100 did not affect the response of macrophage "serum-depleted" cultures to CNI-1493 (i.e., CNI-1493 non-responsive cultures). However, when the filtrate fraction from Centricon®-100 was concentrated by Centricon®-30 ultrafiltration, and added concurrently with CNI-1493, the level of urea and TNF produced from the LPS-stimulated "serum-depleted" macrophage cultures (i.e., CNI-1493 non-responsive) was substantially reduced as compared to identical cultures treated in parallel with CNI-1493 alone. The 30–100 kDa fraction did not affect the level of urea, nitrate, and TNF production from LPS-stimulated RAW 264.7 macrophage cultures proteins not otherwise treated. These data suggest that a 30–100 kDa macrophage cellular protein fraction potentiated or restored the suppressing activity of CNI-1493 on macrophage activation.

Figure 2:
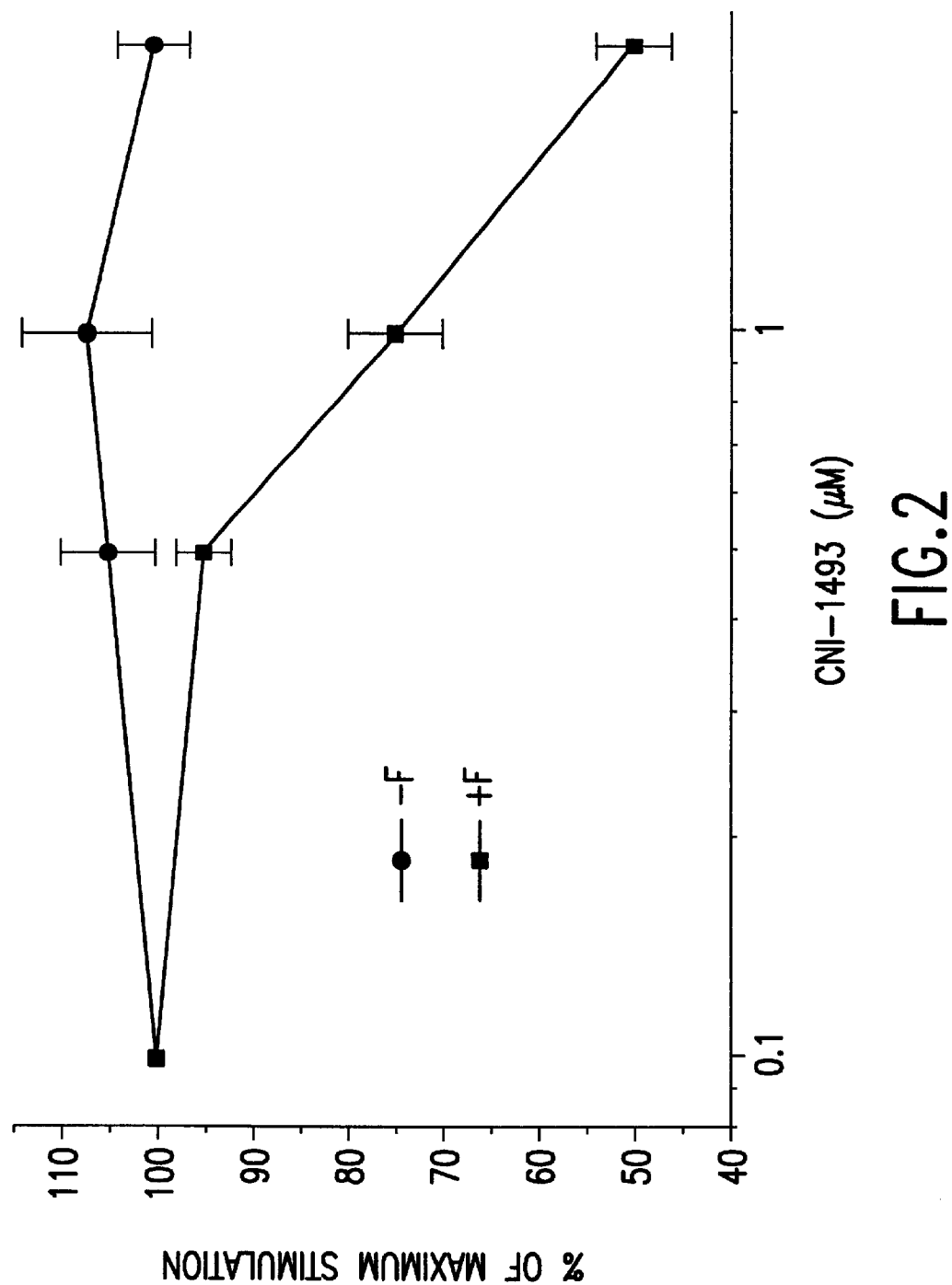
FIG. 2 shows that when the supernatant from responsive cell cultures was added to non-responsive cell cultures, therapeutic activity of CNI-1493 was restored.

We also examined the dose effect of the 30–100 kDa fraction on the suppression of CNI-1493 with respect to urea and TNF production from LPS-stimulated RAW 264.7 macrophage cultures. As shown in FIG. 2, in combination with CNI-1493, the 30–100 kDa fraction promoted a dose-dependent further inhibition of TNF production. In summary, combination treatment with CNI-1493 and the 30–100 kDa fraction provided a >65% total inhibition of LPS-stimulated urea, nitrite, and TNF production from otherwise "non-responsive" RAW 264.7 macrophage cultures.

We further investigated whether CNI-1493-effect-enhancing activity could be isolated from "serum-deprived" non-responsive cells in the corresponding 30–100 kDa macrophage intracellular fraction. The 30–100 kDa fraction from "serum-deprived" or CNI-1493 non-responsive cell cultures did not reveal any activity to potentiate the CNI-1493-mediated inhibition of LPS-induced urea, nitrite, and TNF production by RAW 264.7 macrophage cell cultures. For other cells or tissues examined, including mouse glomerular mesangial cells and mouse crude liver extract (Sigma), no CNI-1493-effect-enhancing activity was detected in the respective 30–100 kDa fractions.

To allow isolation of factor(s) with CNI-1493-effect-enhancing activity from RAW 264.7-conditioned medium, RAW 264.7 cell cultures were split (1:4) into RPMI 1640 containing 10% FBS/1% glutamine, and incubation continued until cultures reached about 80% confluence. Cells were washed twice with pre-warmed OPTI-MEM medium, and then cultured in OPTI-MEM medium (20 ml per 150-mm tissue culture dish) in the presence or absence of LPS at 1 $\mu$g/ml. At specified time points, medium and cells were separately harvested, proteins were fractionated by sequential ultrafiltration through Centricon®-100 and Centricon®-30 filters, as described above, and fractions were subjected to biological assay.

Figure 3:
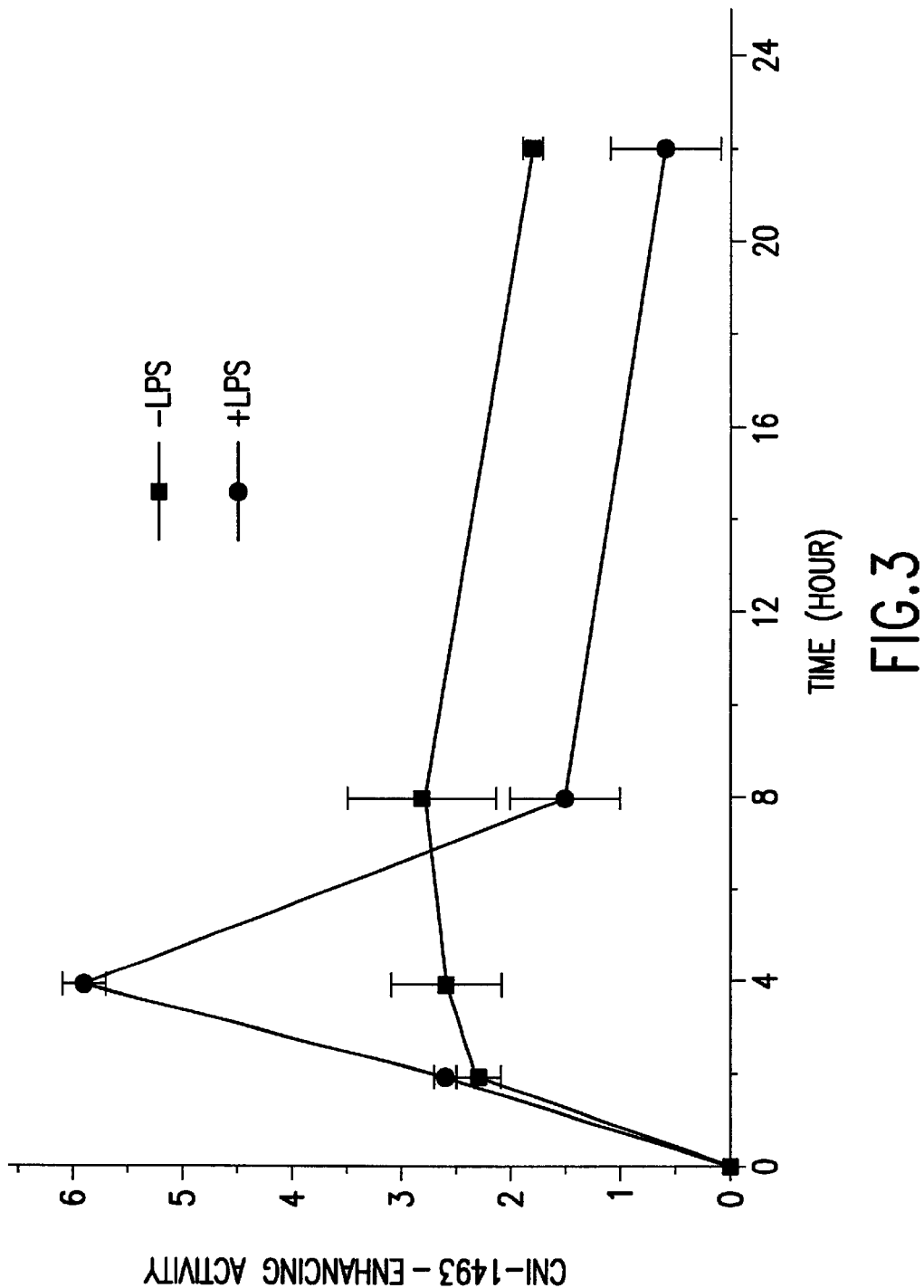
FIG. 3 shows that the accumulation of CNI-1493 activity-enhancing activity or "factor" in cell culture medium is inducible over time. The inducible "factor" (i.e., fetuin) appears in larger amounts within a few hours after challenge with LPS but also appears constitutively.

FIG. 3 shows a time course of accumulation of CNI-1493-effect-enhancing activity in RAW 264.7-conditioned media, where medium and cells were separately harvested and analyzed at each time point. Proteins in medium conditioned by RAW 264.7 cells were concentrated and fractionated by ultrafiltration following the procedure described above and assayed for their CNI-1493-effect-enhancing activity. As shown in FIG. 3, no CNI-1493-effect-enhancing activity was detected in medium that was conditioned for less than 5 minutes ("0 hour" time point). However, a readily detectable level of CNI-1493-effect-enhancing activity was measured in RAW 264.7-conditioned medium by 2 hours. Moreover, at a concentration of 1 $\mu$g/ml, LPS caused a marked increase in CNI-1493-enhancing activity at 4 hours, after which time the rate of accumulation of CNI-1493-effect-enhancing activity markedly declined. Determination of "recoverable" CNI-1493-effect-enhancing activity in the 30–100 kDa intracellular fraction of the corresponding cells revealed a marked decrease in CNI-1493-effect enhancing activity by 4 hours of LPS activation, which corresponded with the increased level of the CNI-1493-effect-enhancing activity observed in the culture medium. These observations suggest that the level of CNI-1493-effect-enhancing activity in macrophage-conditioned culture medium is attributable to constitutive release of protein factor(s) and that this release can be stimulated by LPS treatment.

Figure 5:
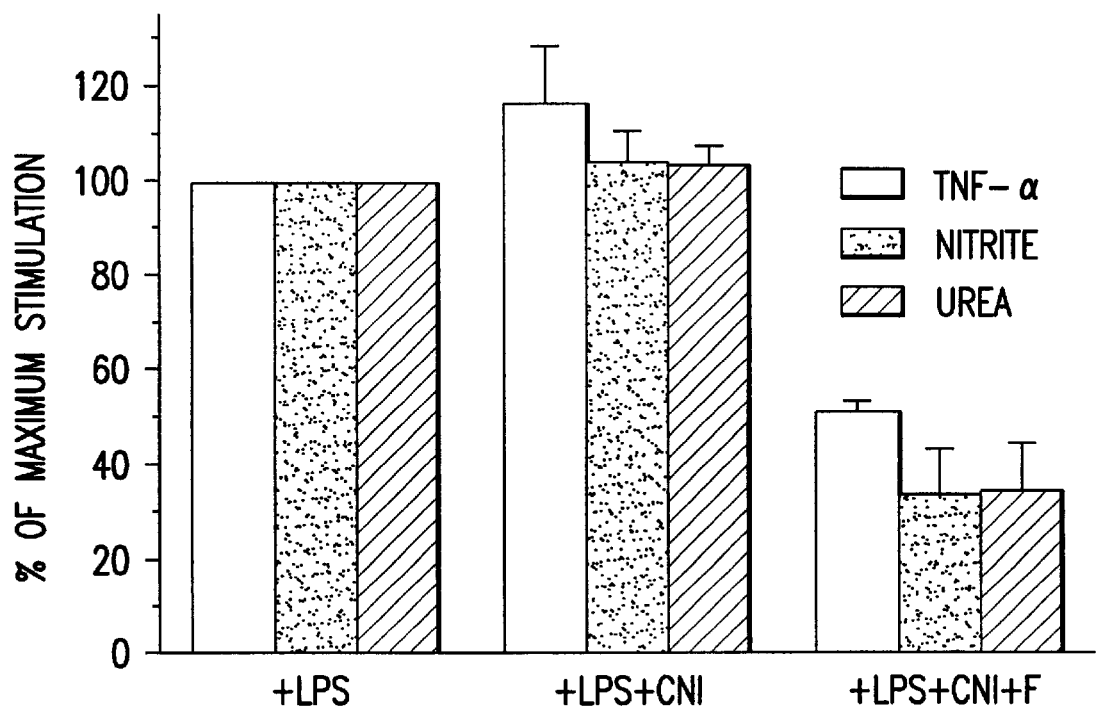
FIG. 5 shows three measures of LPS-stimulated macrophage activation (i.e., production of TNF-α, urea and nitrite) that each independently show an unresponsive state with respect to expected inhibition by compound CNI-1493 and a state of restored responsiveness to compound CNI-1493 when a 30–100 kDa fraction of LPS-stimulated RAW 264.7 cell-conditioned medium was added.
Figure 9:
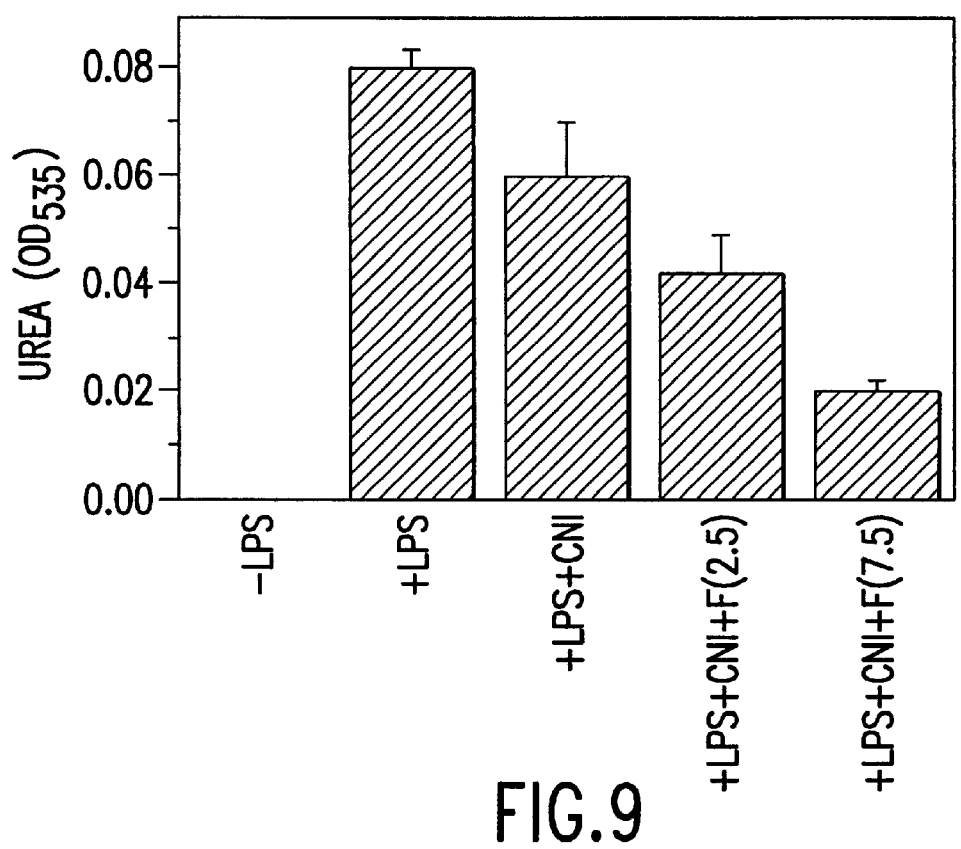
FIG. 9 shows a comparison of urea concentration from LPS-stimulated partially non-responsive cells (or no LPS in the far left bar) showing that the addition of 2.5 μM CNI-1493 showed a small therapeutic activity (measured as a decreased final urea concentration) but that two dose levels of the 30–100 kDa fraction (2.5 μl and 7.5 μl) from LPS-stimulated responsive RAW 264.7 cell cultures increased CNI-1493 therapeutic activity in a concentration-dependent fashion.

Thus, cultured macrophages stimulated with LPS provide a 30–100 kDa protein fraction that potentiates the activity of CNI-1493 to inhibit the production of NO, urea and TNF by these cells in a dose-dependent manner (FIG. 5). The 30–100 kDa fraction itself showed no inhibitory effect on LPS-induced NO, urea and TNF production except in the presence of CNI-1493. FIG. 9 shows a comparison of urea concentration from LPS-stimulated partially non-responsive cells (or no LPS in the far left bar) showing that the addition of 2.5 $\mu$M CNI-1493 showed a small degree of inhibitory activity (i.e., lowering the final urea concentration), but that doses of the 30–100 kDa fraction (2.5 $\mu$l and 7.5 $\mu$l) from LPS-stimulated responsive RAW 264.7 cell cultures increased this CNI-1493 therapeutic activity in a dose-dependent fashion.

Proteins were concentrated from large volumes of RAW 264.7-conditioned media by sequential ultrafiltration on either YM-100, or YM-30 membranes (Amicon Corp., Lexington, Mass.) under $N_2$ at 4° C. with slow stirring.

Figure 6:
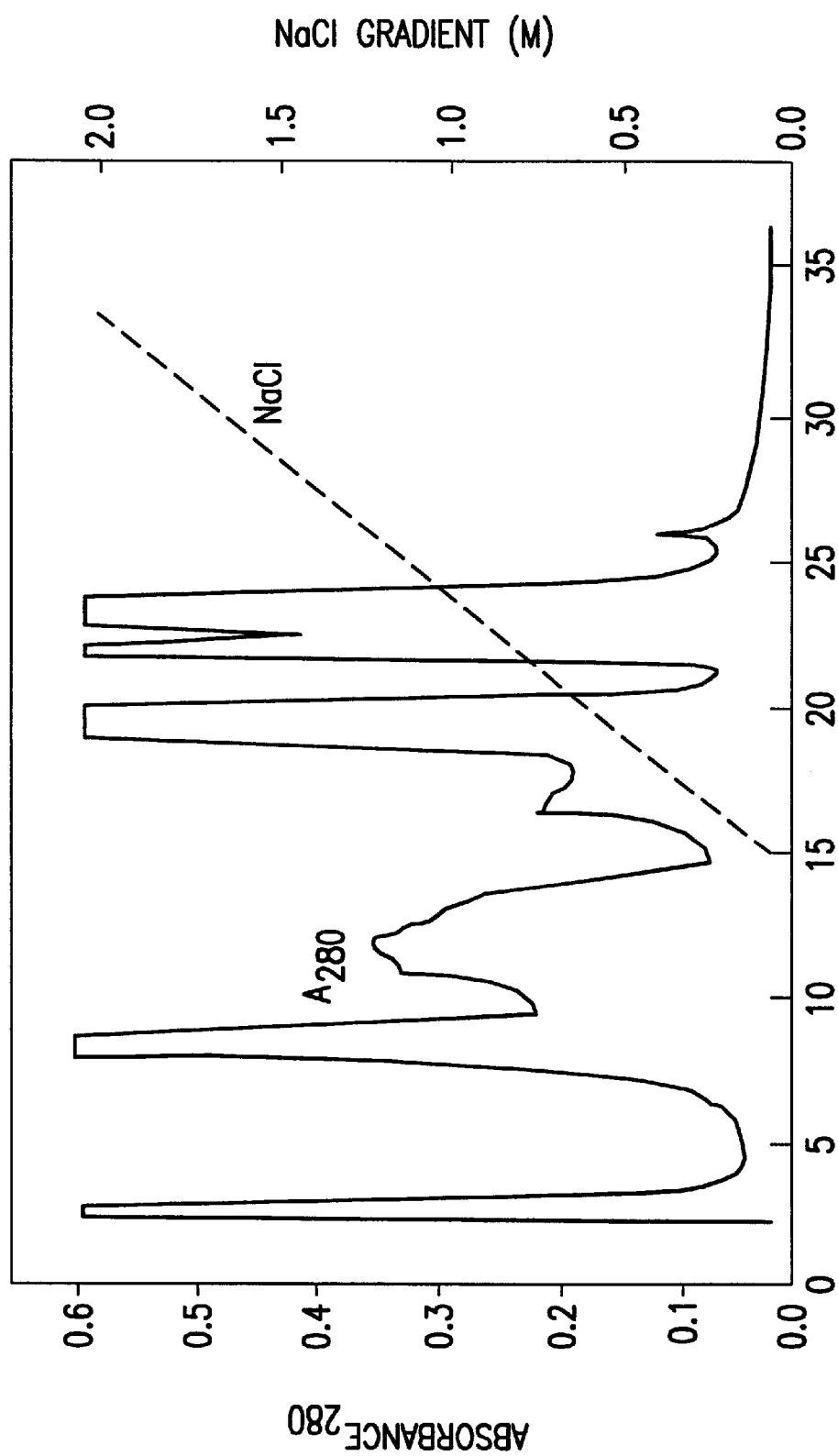
FIG. 6 shows a protein elution profile ($A_{280}$) of LPS-stimulated RAW 264.7 cell culture supernatant (serum-free) over a MONO-Q™ column eluted with NaCl.
Figure 7:
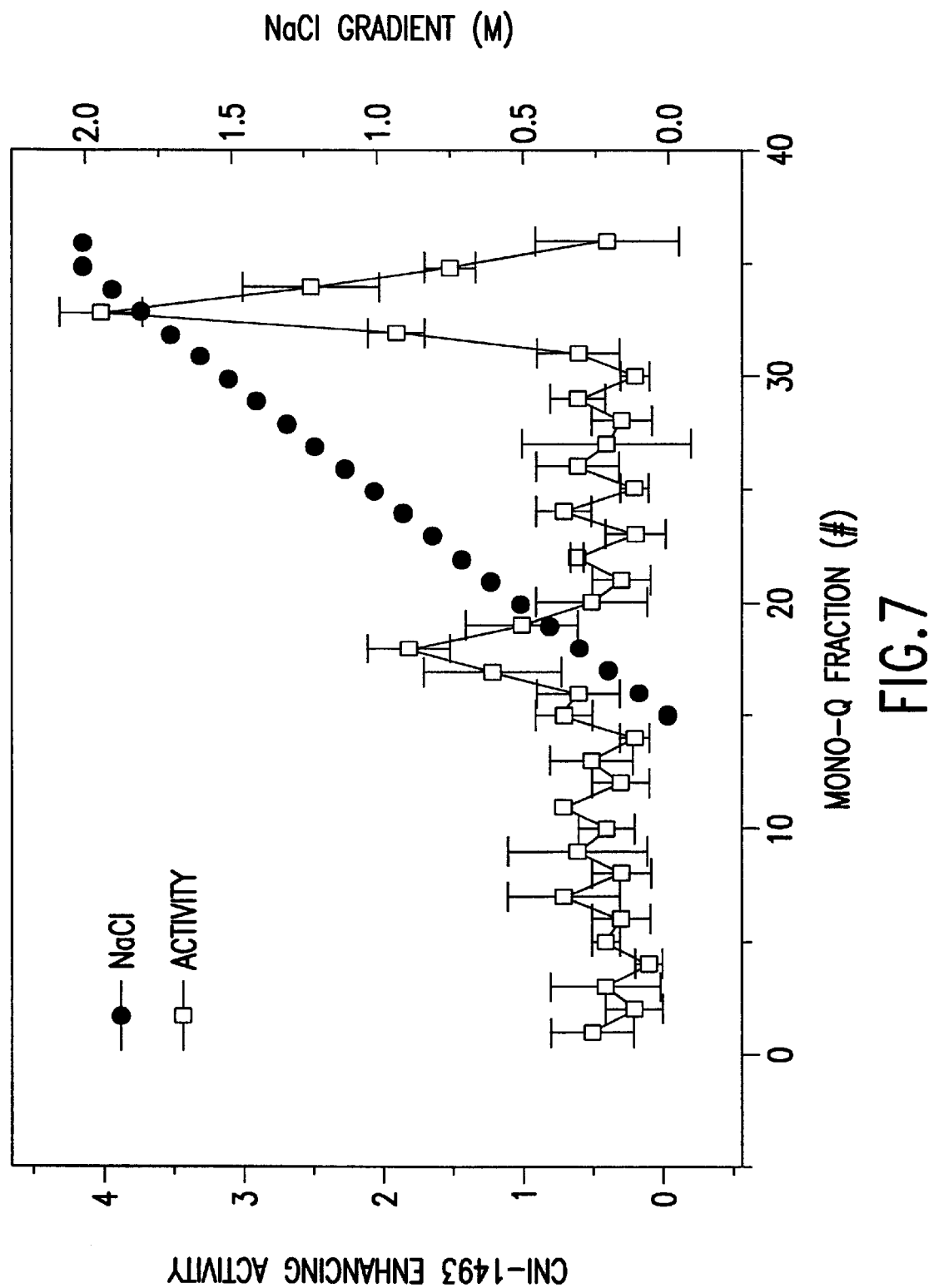
FIG. 7 shows the corresponding activity profile of the FIG. 6 MONO Q™ fractions. Activity was measured in arbitrary Units indicating the relative potency for enhancing the TNF suppressive (i.e., therapeutic) activity of compound CNI-1493 in LPS-stimulated RAW 264.7 cell cultures.

Proteins concentrated either from macrophage intracellular lysates, or from RAW 264.7 cell-conditioned medium were loaded onto a 1-ml MONO-Q® ion exchange column re-equilibrated in buffer "B" (50 mM Tris-HCl, pH 7.5, 150 mM NaCl) at 0.5 ml/min. The ion exchange column was washed with buffer B until the $A_{280}$ dropped below 1% of its maximum (FIG. 6). Bound protein was eluted in 1.0 ml fractions over 25 min with a linear gradient of NaCl increasing to 2 M in buffer B. Fractions were concentrated by Amicon Centricon®-30 ultrafilter, and aliquots were assayed for CNI-1493-effect-enhancing activity, protein content and for polypeptide migration pattern by SDS-PAGE (FIG. 7). Samples were assayed for biological activity at each stage of the preparative sequence.

Protein fractions were mixed with one volume of solubilization buffer (2% SDS, 10% β-mercaptoethanol, 0.03% bromophenol blue, 1.25 M Tris-HCl, pH 7.0), boiled for 5 min, and subjected to electrophoresis on a 4–20% pre-cast gradient SDS-PAGE gel according to the manufacturer's instructions (Bio-Rad). After electrophoresis, the gel was stained either with Coomassie blue or a silver stain using the Silver Plus kit as instructed by the manufacture (Bio-Rad).

Figure 8A:
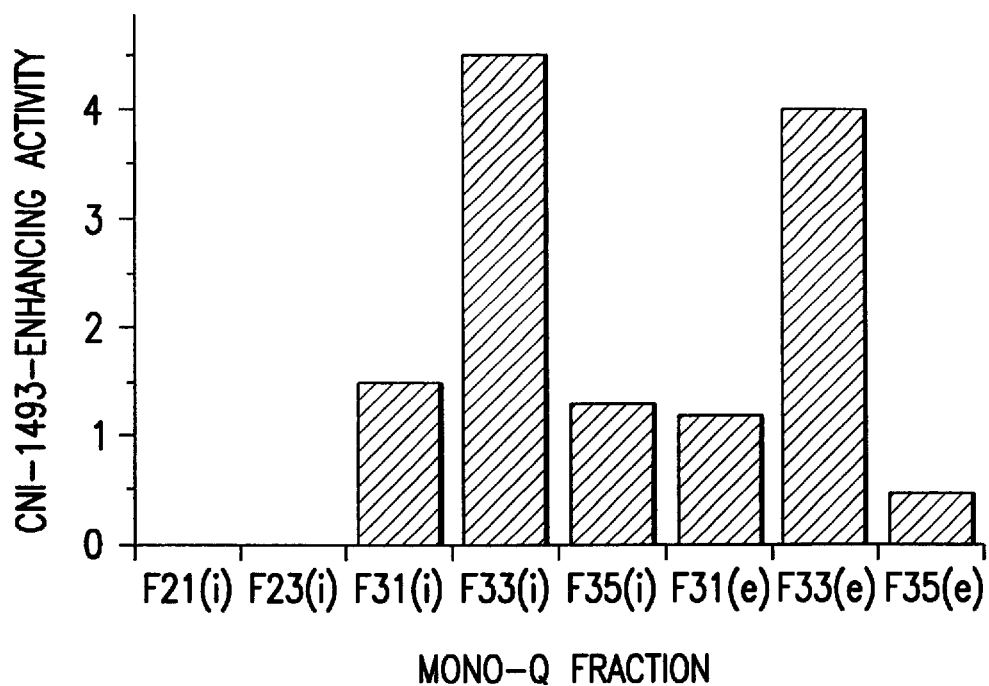
FIG. 8A shows that distinct intracellular and extracellular fractions do or do not enhance CNI-1493 therapeutic activity.
Figure 8B:
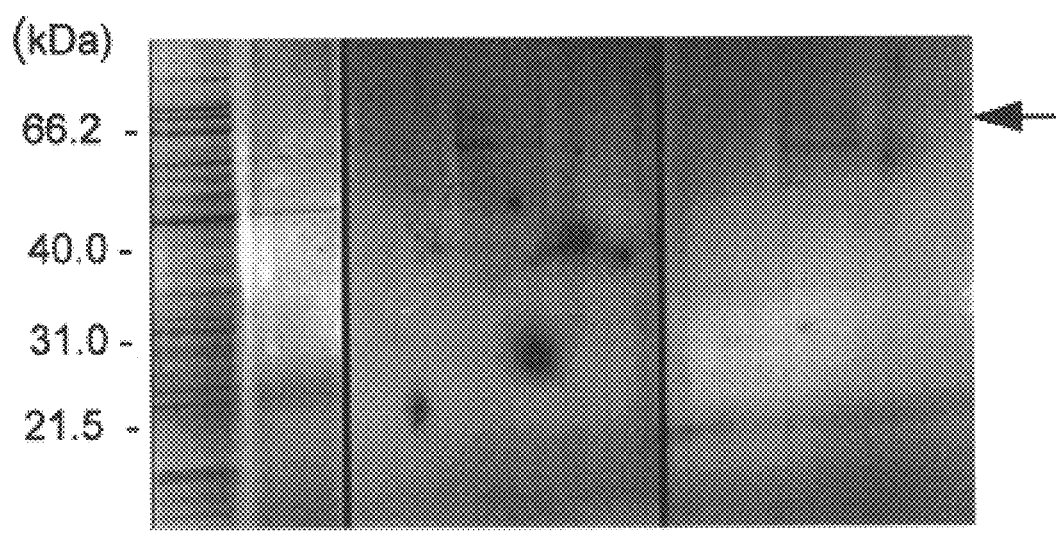
FIG. 8B shows the corresponding SDS-PAGE analysis of the FIG. 8A fractions, emphasizing that enrichment for a single band on the gel correlates with enhancement or restoration of CNI-1493 therapeutic activity.

The molecular weight of protein(s) contributing to the CNI-1493-effect-enhancing activity was determined more precisely under denaturing conditions. MONO-Q® fractions containing CNI-1493-effect-enhancing activity were fractionated on a 10% SDS-PAGE gel. After electrophoresis, gel was evenly sliced (2.0 mm in width) and proteins were eluted from each gel slice (FIG. 8). Briefly, gel slices were rinsed three times with sterile water, once with PBS, crushed into small fragments in 1.0 ml of PBS, and incubated at room temperature overnight with gentle shaking. Gel fragments were subsequently pelleted by a brief centrifugation (2 min, 14,000 rpm), and the isolated proteins were concentrated over a Centricon®-10 filter, and subject to biological assay.

For both macrophage intracellular and extracellular protein fractions, only one peak of CNI-1493-effect-enhancing activity, as revealed by the urea and/or nitrite bioassay, was eluted from the MONO-Q column, between 1.8 to 1.9 M NaCl (FIG. 7). The activity was confirmed both by visual examination of the cultures for cell growth characteristics (i.e., cell counting and culture growth rates), and by TNF ELISA for TNF production. A substantial decrease in number of cells detached from the bottom of plates was consistently observed in wells treated with CNI-1493 and such high-salt fractions. Furthermore, all detectable CNI-1493-effect-enhancing activity was abolished by treatment of high-salt fractions from either macrophage intracellular or extracellular preparations with protease.

The high salt-eluted fraction with the highest CNI-1493-effect-enhancing activity comprised a mixture of materials exhibiting molecular weight species ranging from 90,000 to 7,000 as defined SDS-PAGE analysis with silver staining. Two major polypeptides with the molecular weight of 67 and 57 kDa, respectively, co-eluted with the peak of CNI-1493-effect-enhancing activity. Moreover, two polypeptide bands exhibiting a similar distribution of molecular weights (i.e., ≈57 and 67 kDa) were apparent in SDS-PAGE analysis of fractions isolated from the macrophage intracellular and extracellular protein preparations. That the CNI-1493-effect-enhancing activity in the macrophage intracellular fraction versus the extracellular fraction were attributable to the same protein factor(s), was supported by the observations that the factors co-purify and share (1) the same net charge at pH 7.4, (2) the same molecular weight by ultrafiltration and SDS-PAGE, and (3) the same biological activity profile with respect to restoration of CNI-1493 therapeutic activity. Treatment of the 30–100 kDa ultrafiltrate from both the intracellular and extracellular macrophage preparations with protease abolished CNI-1493-effect-enhancing activity.

Proteins corresponding to the CNI-1493-effect enhancing activity were eluted from the preparative SDS-PAGE gel and subjected to N-terminal sequencing analysis. The N terminal sequence found (SEQ. ID NO. 3) and shown in the top row below as matched to the N-terminal sequence of fetuin (SEQ. ID NO. 4) shown in the bottom row below.

```
Query (SEQ. ID NO.3)      ?PLDPVAGYKEPA?DE?ETEQAALA
                          ||||||||||||| |   |||||||
bovine Fetuin             IPLDPVAGYKEPACDDPDTEQAALA
(SEQ. ID NO.4)
```

EXAMPLE 3

Figure 10:
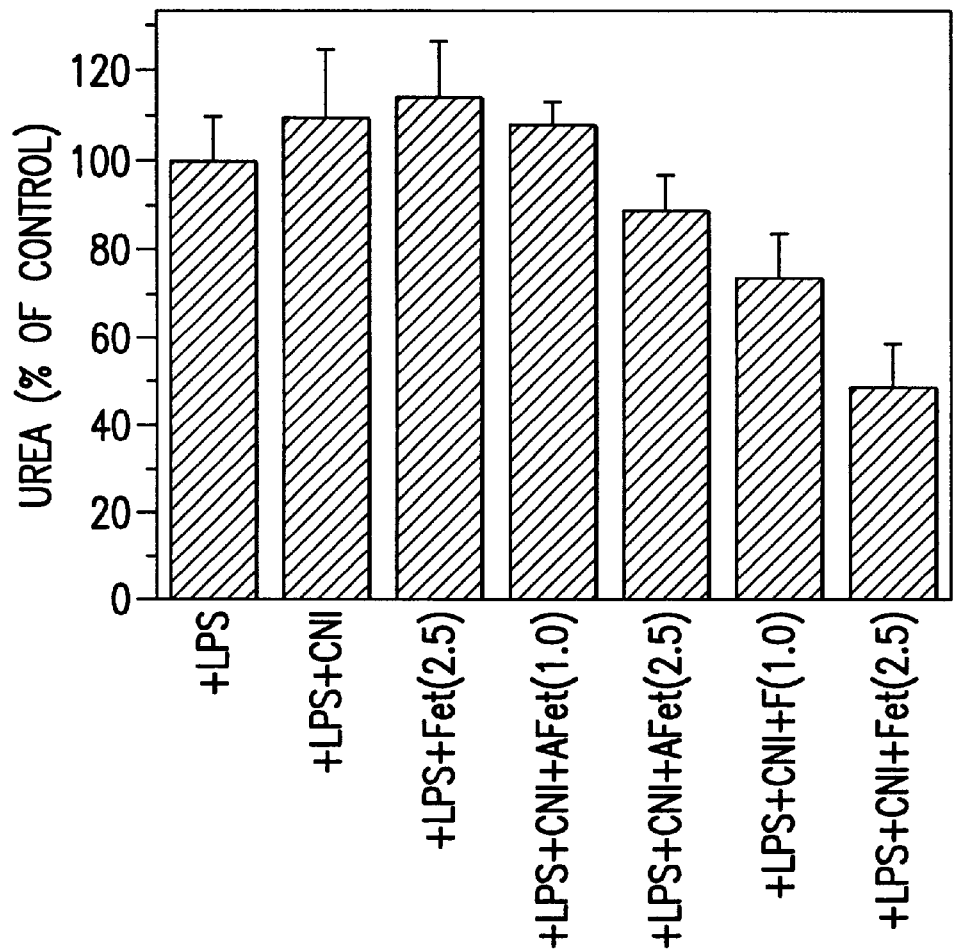
FIG. 10 shows that asialofetuin (fetuin glycoprotein treated to remove terminal sialic acid residues) at concentrations of 1.0 and 2.5 μg/ml was not nearly as active as native fetuin (complete glycoprotein) at the same 1.0 and 2.5 μg/ml concentrations for enhancing CNI-1493 therapeutic activity (measured by suppression of urea production) in LPS-stimulated non-responsive RAW 264.7 cell cultures.

This example illustrates further characterization of the importance of a complex and combination of fetuin or its corresponding human homolog, α2-HS glycoprotein, and a small molecule having a positive charge at physiological pH. CNI-1493 and the genus of structurally related compounds are positively charged at physiological pH by virtue of the presence of multiple guanylhydrazone moieties as provided in the chemical formula herein. Fetuin and α2-HS glycoprotein are negatively charged by virtue of being highly glycosylated and having multiple terminal sialic acid residues in many of the N-linked and O-linked oligosaccharide chains. Therefore, a complex forms between the positively charged small molecule having the guanylhydrazone moiety and the negatively charged sialic acid moieties of fetuin and α2-HS glycoprotein. FIG. 10 shows that asialofetuin (fetuin lacking terminal sialic acid residues), at concentrations of 1.0 and 2.5 μg/ml, was not nearly as active as fetuin at the same 1.0 and 2.5 μg/ml concentrations in enhancing CNI-1493 (2.5 μM) therapeutic activity (measured by suppression of urea production in LPS stimulated non-responsive RAW 264.7 cell cultures).

Figure 11:
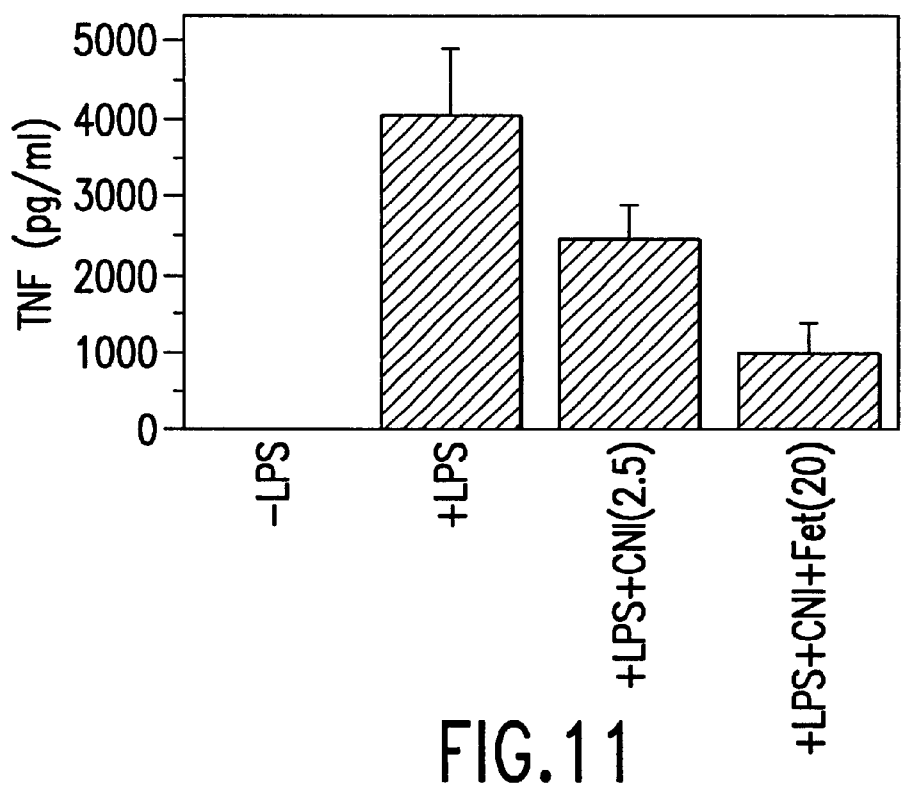
FIG. 11 shows that the therapeutic activity of a low concentration of CNI-1493 (50 nM) to suppress TNF production in LPS-stimulated human PBMCs (peripheral blood mononuclear cells) was enhanced by adding human fetuin glycoprotein (commercially prepared, Sigma), which was supplied at a concentration of 1.0 μg/ml in combination with CNI-1493.

FIG. 11 shows that low concentrations of CNI-1493 (e.g., 50 nM) were active in suppressing TNF production in LPS-stimulated human PBMCs (peripheral blood mononuclear cells) and that this activity was enhanced, in a dose-dependent fashion, by co-administration of bovine fetuin (Sigma) at concentrations of either 1.0 μg/ml or 10 μg/ml along with CNI-1493. These data show the synergistic importance of the inventive combination of the positively charged small molecule compound (in this case a multivalent guanylhydrazone) in combination with the negatively charged fetuin or α2-HS glycoprotein at physiological pH.

Figure 12:
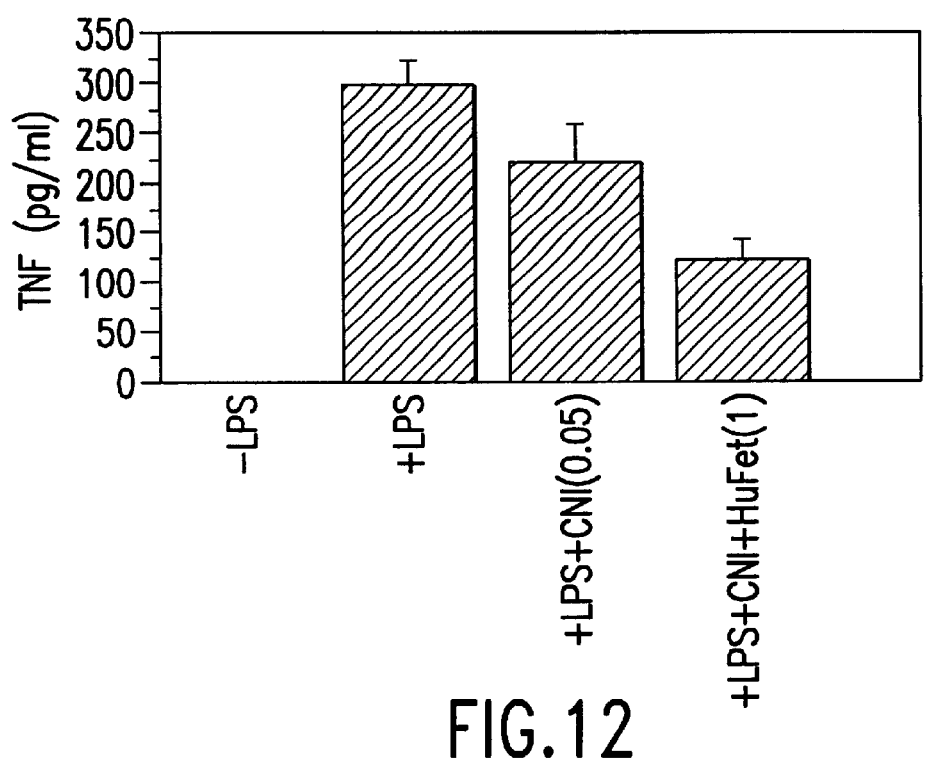
FIG. 12 shows a comparison of CNI-1493 therapeutic activity in LPS-challenged mice as measured by TNF serum levels. Greater therapeutic activity of CNI-1493 is manifest by lower TNF concentrations following LPS challenge. The uniform CNI-1493 dose was 2.5 mg/kg (ip) and the LPS challenge concentration was 13 mg/kg. The fetuin pretreatment dose was 20 mg/kg. These data show that fetuin pretreatment enhanced CNI-1493 therapeutic activity, as measured by suppression of TNF levels.

FIG. 12 shows a comparison of CNI-1493 therapeutic activity in LPS-challenged mice as measured by TNF serum levels. LPS-challenged mice pretreated for 1 hour with bovine fetuin (Sigma) at concentrations of 20 mg/kg in combination with CNI-1493 exhibited lower TNF concentrations following LPS challenge. The CNI-1493 dose was 2.5 mg/kg (ip) and the LPS challenge concentration was 13 mg/kg; serum samples were obtained four hours after LPS challenge. These data show that fetuin pretreatment greatly enhanced CNI-1493 therapeutic activity as measured by suppression of TNF levels in an in vivo model and support the therapeutic importance of the inventive complex and combination in an in vivo predictive therapeutic model.

Figure 13:
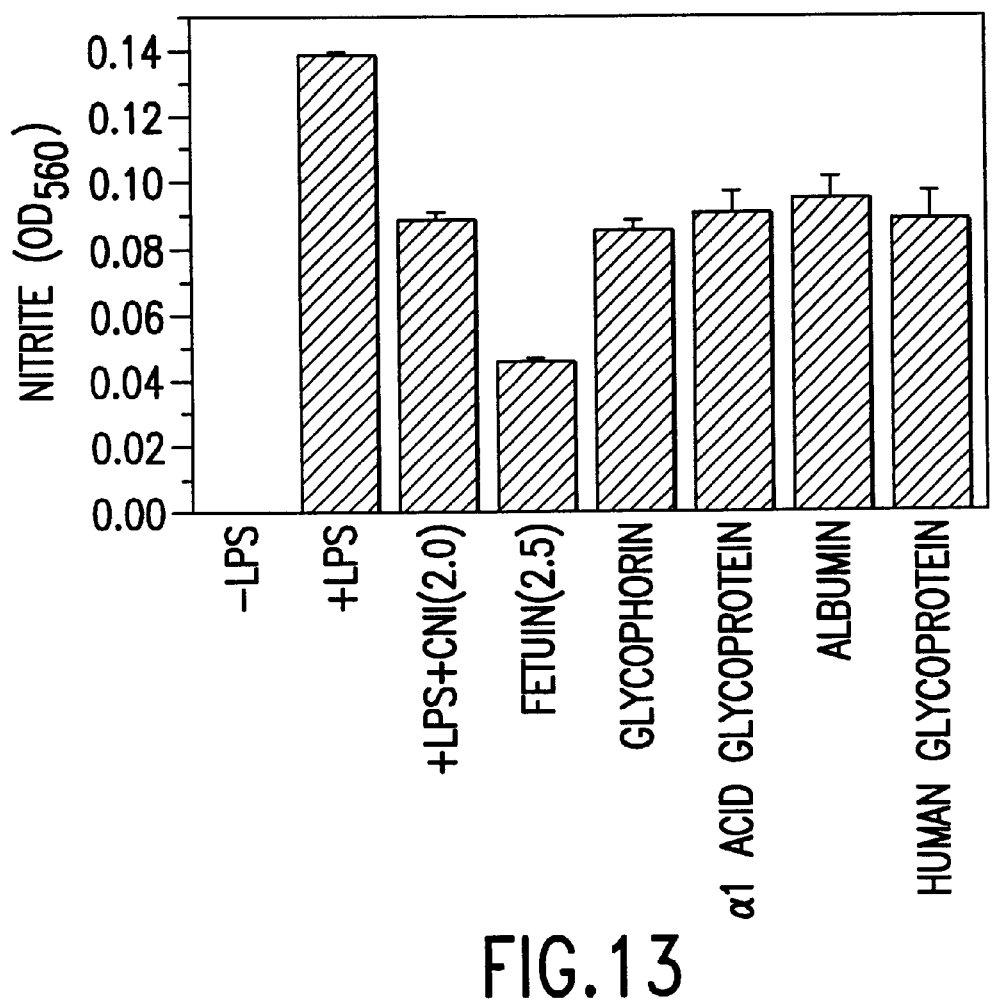
FIG. 13 shows a comparison of CNI-1493 therapeutic activity in RAW 264.7 cells by measuring nitrite production, comparing CNI-1493 alone (2.0 μM concentration for all CNI-1493 doses) versus adding 2.5 μg/ml of fetuin or other glycoproteins (glycophorin, α1-acid glycoprotein, albumin, or human glycoprotein) in combination with CNI-1493. These data show that fetuin was the only glycoprotein tested that was effective for augmenting CNI-1493 therapeutic activity.

FIG. 13 shows a comparison of CNI-1493 activity in RAW cells measuring nitrite production comparing CNI-1493 alone (2.0 μM for all CNI-1493 concentrations) and when adding 2.5 μg/ml of fetuin or other glycoproteins (glycophorin, α1-acid glycoprotein, albumin, or human glycoprotein). These other glycoproteins are also net negatively charged at physiological pH. These data show that only fetuin was effective in augmenting CNI-1493 therapeutic activity, proving the specific importance of fetuin and α2-HS glycoprotein, as opposed to other net negatively charged glycoproteins.

EXAMPLE 4

This example illustrates the utility of the present invention to, on the one hand, identify and isolate therapeutically active small molecule compounds having a net positive charge at physiological pH, and, on the other hand, to identify and isolate proteins or other biomolecules that bind to such therapeutic small molecules. In a first instance, a mammalian fetuin glycoprotein or a combination or mixture of mammalian fetuin glycoproteins, including for instance human fetuin glycoprotein or α2-HS glycoprotein, wherein the fetuin glycoproteins preferably are in a native conformation and the fetuin glycoprotein oligosaccharide moieties preferably contain a plurality of sialic acid residues, is provided in a buffer solution at physiologic pH. To this solution is added a solution of a small molecule compound or a library or mixture of multiple small molecule compounds such that the small molecule compounds contact the fetuin glycoproteins at physiological pH and can form complexes therewith. The fetuin/compound contacting solution is then fractionated into a high molecular weight fraction (comprising the fetuin and any fetuin/compound complexes) and a low molecular weight fraction (containing uncomplexed small molecule compounds), for instance by size exclusion chromatography or filtration over a 30 kDa cut-off ultrafilter. The low molecular weight fraction is then assayed, for instance spectrophotometrically at UV wavelengths, to determine the concentration of the small molecule compounds remaining, and this measure is compared to a control sample subject to an identical protocol but conducted in the absence of the fetuin glycoproteins. A decrease in the concentration of the small molecule compounds in the low molecular weight fraction relative to the control indicates binding and/or complexation of the small molecule compounds with the fetuin glycoprotein and consequent partitioning of the small molecule compound together with fetuin into the high molecular weight fraction.

Particularly in the case where this method is used to screen a library of chemically diverse small molecule compounds for binding to fetuin glycoprotein, the small molecule compounds then are separated from fetuin, for instance by extraction into a non-aqueous solvent, changing the pH, addition of a salt or a chaotropic agent, or other means known in the art, optionally followed by a fractionation procedure based on molecular weight (as described above) and the thereby isolated small molecule compounds are characterized to identify their chemical structure. In this regard, any of the physical and chemical techniques known in the art to characterize small molecule compounds are used, including for example, liquid, gas, high performance and thin layer chromatography; infrared, UV/vis, mass, high resolution mass and nuclear magnetic resonance spectroscopy; and various coupled methods such as GC-MS or HPLC-MS. The isolated small molecule compounds are then assayed to provide a profile of their biological activity.

Alternative embodiments are also contemplated, including for instance the embodiment in which the fetuin glycoprotein is immobilized by covalent attachment to a solid support or matrix, for instance an activated Sepharose bead such as CNBr-Sepharose, according to techniques well known in the art. This immobilization serves to facilitate separation of uncomplexed small molecule compounds, by washing the fetuin-derivatized matrix in buffer, from those small molecule compounds which bind or complex with fetuin during the contacting step. Subsequently, the bound or complexed small molecules compounds are eluted from the immobilized fetuin as described above and characterized as to their chemical structure and biological activity profile. As practiced, these methods allow the identification of useful small molecule compounds with therapeutic utility based on their binding to fetuin glycoprotein. These methods also provide means to screen libraries of small molecule compounds, including for instance combinatorial libraries or the mixed products of various synthetic combinatorial chemistry techniques and methods, for such useful therapeutic compounds.

Yet another embodiment of the present invention provides a small molecule compound immobilized on a solid support or matrix, which derivatized matrix is contacted with a solution of proteins and/or glycoproteins or other molecular species with suspected binding activity for the small molecule compound of interest at physiological pH. After allowing a period for binding interactions to occur during the contacting step, the matrix is flushed with buffer and bound proteins are eluted and collected as described above. These isolated binding partners are then characterized by chemical and physical techniques summarized above and others well-known in the art to provide information about the chemical nature of proteins, glycoproteins and other biomolecules, such as amino acid composition analysis and amino acid sequencing. These binding assays are useful to screen potential drug compounds whose therapeutic activity can be augmented by either co-administration with fetuin or by forming a drug-fetuin complex prior to administration; and further, to identify other proteins, glycoproteins or biomolecules that enhance the therapeutic activity of small molecule compounds when co-administered therewith as a combination or a complex.

We claim:

1. A complex comprising:
   a glycosylated polypeptide selected from the group consisting of mammalian fetuin, α2-HS glycoprotein, and combinations therof; and
   a positively charged (at physiological pH) therapeutic compound selected from the formula:

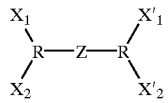

wherein R is independently selected from the group consisting of phenyl, pyridine, amino-substituted pyridine, purine, oxo-substituted purine, $C_{1-6}$ alkyl-substituted purine, xanthine, pyrimidine, $C_{1-6}$ alkyl-substituted pyrimidine, and oxo-substituted pyrimidine; wherein $X_2$ is selected from the group consisting of $H_2N(CNH)$—NH—N═CH—, $H_2N(CNH)$—NH—N═C($CH_3$)—, and H—; wherein $X_1$, $X'_1$ $X'_2$ are independently selected from the group consisting of $H_2N(CNH)$—NH—N═CH— and $H_2N(CNH)$—NH—N═C($CH_3$)—; wherein Z is selected from the group consisting of phenyl, pyridyl ($C_5NH_3$), —NH(CO)NH—, straight or branched $C_{2-10}$ alkyl, straight or branched $C_{2-10}$ alkenyl, —A— straight or branched $C_{2-10}$ alkyl —A—, —A— straight or branched $C_{2-10}$ alkenyl —A—, and —A—, wherein A is independently selected from the group consisting of —NH(CO)—, —(CO)NH—, —NH(CO)NH—, —NH—, and —O—.

2. The complex of claim 1 wherein the glycosylated polypeptide is human fetuin.

3. The complex of claim 1 wherein $X_1$, $X'_1$, $X_2$ and $X'_2$ are each $H_2N(CNH)$—NH—N═C($CH_3$)—.

4. A pharmaceutical composition comprising:
   (A) an active component consisting essentially of glycosylated polypeptide selected from the group consisting of a mammalian fetuin, α-2-HS glycoprotein, and combinations thereof; and
   (B) a positively charged (at physiological pH) therapeutic compound selected from the formula:

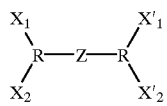

wherein R is independently selected from the group consisting of phenyl, pyridine, amino-substituted pyridine, purine, oxo-substituted purine, $C_{1-6}$ alkyl-substituted purine, xanthine, pyrimidine, $C_{1-6}$ alkyl-substituted pyrimidine, and oxo-substituted pyrimidine; wherein $X_2$ is selected from the group consisting of $H_2N(CNH)$—NH—N═CH—, $H_2N(CNH)$—NH—N═C($CH_3$)—, and H—; wherein $X_1$, $X'_1$ $X'_2$ are independently selected from the group consisting of $H_2N(CNH)$—NH—N═CH— and $H_2N(CNH)$—NH—N═C($CH_3$)—; wherein Z is selected from the group consisting of phenyl, pyridyl ($C_5NH_3$), —NH(CO)NH—, straight or branched $C_{2-10}$ alkyl, straight or branched $C_{2-10}$ alkenyl, —A— straight or branched $C_{2-10}$ alkyl —A—, —A— straight or branched $C_{2-10}$ alkenyl —A—, and —A—, wherein A is independently selected from the group consisting of —NH(CO)—, —(CO)NH—, —NH(CO)NH—, —NH—, and —O—; and
   (C) a pharmaceutically acceptable carrier.

5. The pharmaceutical composition of claim 4 wherein the glycosylated polypeptide is human fetuin.

6. The pharmaceutical composition of claim 4 wherein $X_1$, $X'_1$, $X_2$ and $X'_2$ are each $H_2N(CNH)$—NH—N═C($CH_3$)—.

7. A therapeutic combination of glycosylated polypeptide and a positively charged (at physiological pH) therapeutic compound:
   wherein the glycosylated polypeptide is selected from the group consisting of a mammalian fetuin, α2-HS glycoprotein, and combinations thereof; and
   wherein the positively charged (at physiological pH) therapeutic compound is selected from the formula:

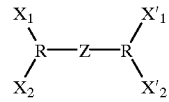

wherein R is independently selected from the group consisting of phenyl, pyridine, amino-substituted pyridine, purine, oxo-substituted purine, $C_{1-6}$ alkyl-substituted purine, xanthine, pyrimidine, $C_{1-6}$ alkyl-substituted pyrimidine, and oxo-substituted pyrimidine; wherein $X_2$ is selected from the group consisting of $H_2N(CNH)$—NH—N═CH—, $H_2N(CNH)$—NH—N═C($CH_3$)—, and H—; wherein $X_1$, $X'_1$ $X'_2$ are independently selected from the group consisting of $H_2N(CNH)$—NH—N═CH— and $H_2N(CNH)$—NH—N═C($CH_3$)—; wherein Z is selected from the group consisting of phenyl, pyridyl ($C_5NH_3$), —NH(CO)NH—, straight or branched $C_{2-10}$ alkyl, straight or branched $C_{2-10}$ alkenyl, —A— straight or branched $C_{2-10}$ alkyl —A—, —A— straight or branched $C_{2-10}$ alkenyl —A—, and —A—, wherein A is independently selected from the group consisting of —NH(CO)—, —(CO)NH—, —NH(CO)NH—, —NH—, and —O—.

8. The therapeutic combination of claim 7 wherein the glycosylated polypeptide is human fetuin.

9. The therapeutic combination of claim 7 wherein $X_1$, $X'_1$, $X_2$ and $X'_2$ are each $H_2N(CNH)$—NH—N═C($CH_3$)—.

* * * * *